(12) United States Patent
Seip et al.

(10) Patent No.: US 11,278,339 B2
(45) Date of Patent: Mar. 22, 2022

(54) SYSTEM AND METHOD FOR TREATING TISSUE, FLUID MANAGEMENT SYSTEM, AND ULTRASOUND SYSTEM INCLUDING AND/OR FOR USE WITH SAME

(71) Applicant: SONACARE MEDICAL, LLC, Charlotte, NC (US)

(72) Inventors: Ralf Seip, Charlotte, NC (US); Rodrigo Chaluisan, Charlotte, NC (US); Laura Court, Charlotte, NC (US); Mark Carol, Charlotte, NC (US)

(73) Assignee: SONABLATE CORP., Charlotte, NC (US)

( * ) Notice: Subject to any disclaimer, the term of this patent is extended or adjusted under 35 U.S.C. 154(b) by 1133 days.

(21) Appl. No.: 15/842,778

(22) Filed: Dec. 14, 2017

(65) Prior Publication Data
US 2018/0161603 A1  Jun. 14, 2018

Related U.S. Application Data

(60) Provisional application No. 62/560,334, filed on Sep. 19, 2017, provisional application No. 62/433,989, filed on Dec. 14, 2016.

(51) Int. Cl.
*A61B 18/00* (2006.01)
*A61B 8/00* (2006.01)
(Continued)

(52) U.S. Cl.
CPC ............ *A61B 18/00* (2013.01); *A61B 8/546* (2013.01); *B01D 19/0031* (2013.01);
(Continued)

(58) Field of Classification Search
None
See application file for complete search history.

(56) References Cited

U.S. PATENT DOCUMENTS 7,052,463 B2   5/2006 Peszynski et al.
7,559,905 B2   7/2009 Kagosaki et al.
(Continued)

OTHER PUBLICATIONS

International Search Report and Written Opinion in International Application No. PCT/US2017/066531, dated Feb. 14, 2018.

*Primary Examiner* — Jason M Greene
(74) *Attorney, Agent, or Firm* — Mark T. Vogelbacker; Eckert Seamans Cherin & Mellott, LLC

(57) ABSTRACT

A fluid management system for use with an ultrasound probe assembly can include first and second conduits each configured to extend from and be fluidly connected to the ultrasound probe assembly. A fluid directing system can include a circulation pump fluidly connected to both the first and second conduits. A fluid degassing system can be fluidly connected to the first and second conduits. The fluid degassing system can be configured to remove at least some gas from the fluid in the ultrasound probe assembly. A temperature control system can be fluidly connected to the first and second conduits. The temperature control system can be configured to control the temperature of the fluid in the ultrasound probe assembly. A volume adjustment system can be fluidly connected to the first and second conduits. The volume adjustment system can be configured to adjust the volume of the fluid in the ultrasound probe assembly.

22 Claims, 12 Drawing Sheets

(51) Int. Cl.
  *B01D 19/00*   (2006.01)
  *A61N 7/00*    (2006.01)
  *A61B 90/98*   (2016.01)
  *A61B 90/96*   (2016.01)

(52) U.S. Cl.
  CPC .............. *A61B 90/96* (2016.02); *A61B 90/98* (2016.02); *A61B 2018/00011* (2013.01); *A61N 7/00* (2013.01)

(56) References Cited

U.S. PATENT DOCUMENTS

| | | | |
|---|---|---|---|
| 2004/0059226 A1* | 3/2004 | Peszynski | A61B 8/546 600/459 |
| 2006/0158956 A1 | 7/2006 | Laugharn, Jr. et al. | |
| 2008/0077056 A1* | 3/2008 | Kagosaki | A61N 7/02 601/2 |
| 2011/0259466 A1 | 10/2011 | Tasard et al. | |
| 2014/0196607 A1 | 7/2014 | Seip et al. | |
| 2014/0243677 A1 | 8/2014 | Johnson et al. | |
| 2016/0236013 A1 | 8/2016 | Carol et al. | |

\* cited by examiner

SYSTEM AND METHOD FOR TREATING TISSUE, FLUID MANAGEMENT SYSTEM, AND ULTRASOUND SYSTEM INCLUDING AND/OR FOR USE WITH SAME

CROSS-REFERENCE TO RELATED APPLICATION

This application claims priority to U.S. Provisional Application No. 62/433,989, filed Dec. 14, 2016 and titled "Robotic Therapeutic Ultrasound System and Method," which is herein incorporated by reference. This application also claims priority to U.S. Provisional Application No. 62/560,334, filed Sep. 19, 2017 and titled "Single-Use Single-Loop Fluid and Method of Making and Using Same," which is herein incorporated by reference.

FIELD

In one embodiment, the presently disclosed technology relates generally to fluid management systems for use with ultrasound probe assemblies. In another embodiment, the presently disclosed technology also relates generally to ultrasound systems including fluid management systems.

In one embodiment, the presently disclosed technology is generally directed to a compact, single, fluid circuit coupled to an ultrasound probe assembly. Optionally, the circuit can form part of and/or be removably attachable to a fluid management system.

BACKGROUND

It is known to use therapeutic ultrasound in a clinical setting for the treatment of a multitude of diseases and conditions in a non-invasive or minimally invasive manner One such example is described in U.S. Patent Application Publication No. 2014/0243677. In therapeutic ultrasound systems, coupling the ultrasound energy from the ultrasound transducer assembly of the ultrasound probe assembly to the patient is typically accomplished through a water-filled conformal bolus assembly of the ultrasound probe assembly. One such prior art system is described in U.S. Pat. No. 7,559,905 ("the '905 patent"), which is herein incorporated by reference. The system of the '905 patent includes two fluid circuits connected by a fluid reservoir. In operation, managing the fluid volume or fluid connection of ultrasound systems in a simple and effective way is often overlooked or neglected, resulting in the development of systems that are cumbersome and complicated to use.

Preparing therapeutic ultrasound systems for use typically includes installing an apparatus that transports the coupling fluid (e.g., water) to the probe, and priming and filling the bolus and fluid path. This task is typically performed by technical support staff who may not necessarily be aware of the many nuances associated with being able to correctly and reliably deliver ultrasound energy from the transducer assembly through a fluid volume and into the patient. The increasing use of therapeutic ultrasound in a sterile operating room environment also adds additional requirements to the ability of the user to maintain the sterility of the water used for transducer/patient coupling, complicating treatment delivery.

SUMMARY

In light of the above-described and other drawbacks of the prior art, there is room for improvement in fluid management systems and in ultrasound systems including the same. Embodiments of the presently disclosed technology overcome certain drawbacks of prior art designs and satisfy the above-outlined and other objectives.

As one aspect of the presently disclosed technology, a fluid management system for use with an ultrasound probe assembly is provided. The system includes a plurality of conduits including a first conduit and a second conduit each configured to extend from and be fluidly connected to the ultrasound probe assembly, a fluid directing system having a first pump fluidly connected to both the first conduit and the second conduit in order to circulate a fluid into and out of the ultrasound probe assembly, the first pump being a circulation pump, a fluid degassing system fluidly connected to the first and second conduits, the fluid degassing system being configured to remove at least some gas from the fluid in the ultrasound probe assembly, a temperature control system fluidly connected to the first and second conduits, the temperature control system being configured to control the temperature of the fluid in the ultrasound probe assembly, and a volume adjustment system fluidly connected to the first and second conduits, the volume adjustment system being configured to adjust the volume of the fluid in the ultrasound probe assembly.

As another aspect of the presently disclosed technology, an ultrasound system is provided. The ultrasound system includes an ultrasound probe assembly and a fluid management system. The ultrasound probe assembly has a transducer assembly and a bolus assembly. The bolus assembly surrounds at least a portion of the transducer assembly. The fluid management system includes a plurality of conduits including a first conduit and a second conduit each extending from and being fluidly connected to the ultrasound probe assembly, a fluid directing system having a first pump fluidly connected to both the first conduit and the second conduit in order to circulate a fluid into and out of the ultrasound probe assembly, the first pump being a circulation pump, a fluid degassing system fluidly connected to the first conduit and second conduits, the fluid degassing system being configured to remove at least some gas from the fluid in the ultrasound probe assembly, a temperature control system fluidly connected to the first and second conduits, the temperature control system being configured to control the temperature of the fluid in the ultrasound probe assembly, the temperature control system including a temperature sensor, a heating element, or cooling element (or both), and a heat exchanger module coupled to the heating/cooling element(s), the heat exchanger module being fluidly connected to the circulation pump, and a volume adjustment system fluidly connected to the first and second conduits. The volume adjustment system is configured to adjust the volume of the fluid in the ultrasound probe assembly. The temperature sensor is connected to the ultrasound probe assembly and is configured to cooperate with the heating/cooling element(s) in order to control the temperature of the fluid in the ultrasound probe assembly.

In another embodiment, the presently disclosed technology is directed to a single loop, closed, disposable (i.e., single-use) fluid path that includes interconnect tubing, an inline degasser cartridge, an inline heat exchanger block, a fluid reservoir (empty or pre-filled), and an inline dissolved $O_2$ sensor. In some instantiations, a disposable bolus can also form part of and/or be removably attachable to the single-use components, thereby further simplifying setup of an ultrasound system.

In yet another embodiment, the presently disclosed technology is directed to a single circuit fluid loop that is compatible with one or more of the fluid management systems and/or the ultrasound probe assemblies shown and described herein. In one embodiment, the single-use, single-loop, single-use fluid loop kit can be an integral part of the coupling fluid management system of any therapeutic ultrasound system, regardless of whether this system utilizes high intensity focused ultrasound ("HIFU"), hyperthermia, non-ablative ultrasound, etc., and utilizing either extracorporeal ultrasound applicators, intracorporeal applicators, or intracavity ultrasound applicators.

BRIEF DESCRIPTION OF THE DRAWINGS

The foregoing summary, as well as the following detailed description of the presently disclosed technology, will be better understood when read in conjunction with the appended drawings. For the purpose of illustrating the presently disclosed technology, there are shown in the drawings various illustrative embodiments. It should be understood, however, that the presently disclosed technology is not limited to the precise arrangements and instrumentalities shown. In the drawings.

DETAILED DESCRIPTION

Figure 1A:
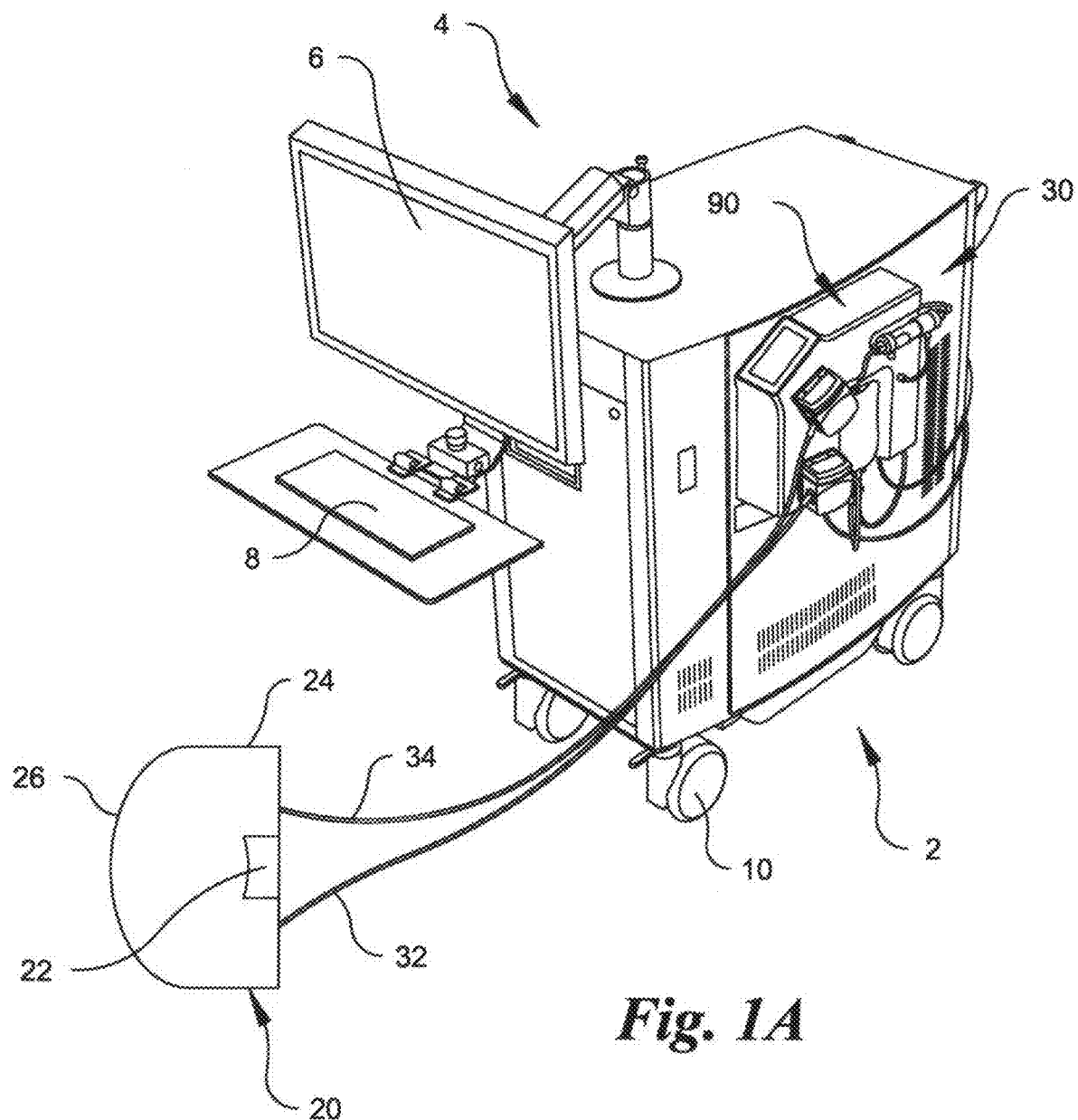
FIG. 1A is partially simplified perspective view of an ultrasound system according to one embodiment of the presently disclosed technology.

While systems, apparatus and methods are described herein by way of examples and embodiments, those skilled in the art recognize that the systems, apparatus and methods of the presently disclosed technology are not limited to the embodiments or drawings described. It should be understood that the drawings and description are not intended to be limited to the particular form disclosed. Rather, the presently disclosed technology covers all modifications, equivalents and alternatives falling within the spirit and scope of the appended claims. Any headings used herein are for organizational purposes only and are not meant to limit the scope of the description or the claims.

As used herein, the words "is" and "may" are used in a permissive sense (i.e., meaning having the potential to) rather than the mandatory sense (i.e., meaning must). As employed herein, the term "number" shall mean one or an integer greater than one (i.e., a plurality). Similarly, the words "include," "including," and "includes" mean including, but not limited to. Unless specifically set forth herein, the terms "a," "an" and "the" are not limited to one element but instead should be read as meaning "at least one." The terminology includes the words noted above, derivatives thereof and words of similar import.

As described below, various embodiments of the presently disclosed technology may be readily combined or even omitted. While the presently disclosed technology is described with reference to ultrasound or HIFU, the presently disclosed technology is not so limited and has applicability to other fields and uses. Furthermore, like elements among different embodiments are identified with one or more prime symbols (') after like reference numerals. Description of similar or identical features between the embodiments may be omitted herein for the sake of brevity and convenience only.

The therapeutic ultrasound industry and end-user(s) could benefit from a fluid management system and associated components (such as a conformal bolus and a simple, cost-effective fluid loop) that addresses the various shortcomings of current implementations. For example, while the system of the '905 patent has proven to be beneficial, it would be beneficial to employ a fluid path or system that is less complicated, easier for a user to set-up in an operating or medical examination room, and cheaper (e.g., due to less components).

1. Embodiments of Fluid Management System

One way to solve the drawback(s) of the prior art is to provide or use a fluid management system that is configured to (i) automatically fill (i.e., prime) an entire fluid path (e.g., a fluid path including at least an ultrasound probe assembly), (ii) automatically circulate fluid through the fluid path to support functions of the fluid management system and the ultrasound probe assembly, (iii) provide a temperature control system to cool/heat the ultrasound probe assembly, (iv) automatically remove at least some gas from fluid in the fluid path to allow for ultrasound energy to travel from the transducer assembly through the coupling fluid and into the patient without impedance of gas bubbles, and/or (v) provide the user with the ability to adjust the fluid volume in the ultrasound probe assembly. The fluid management system(s) of the presently disclosed technology achieves the above-described benefits in a relatively sterile environment, and is/are advantageously able to be used by operating personnel without requiring significant training and setup time.

Figure 1B:
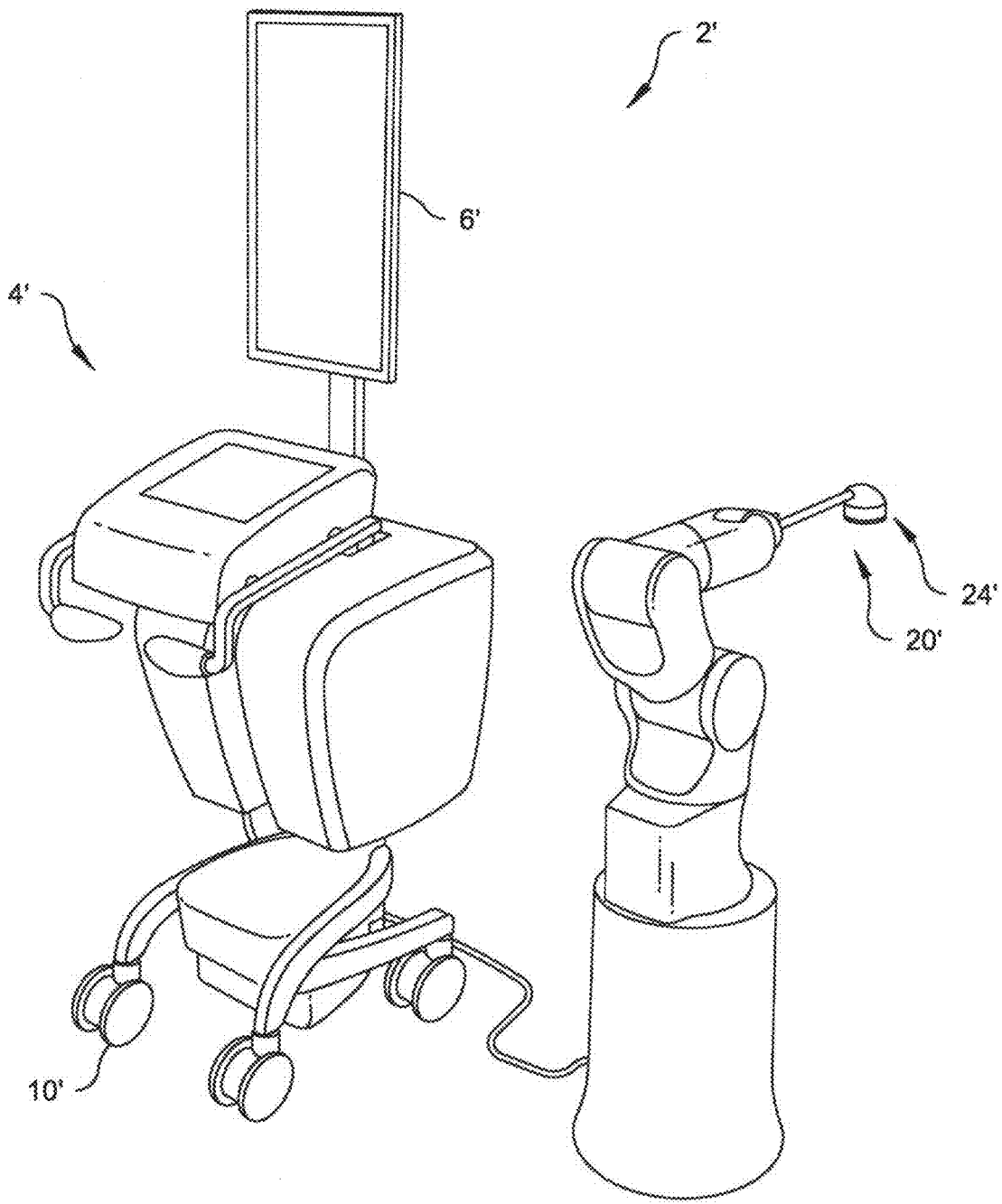
FIG. 1B is a partially simplified perspective view of an ultrasound system according to another embodiment of the presently disclosed technology.
Figure 2:
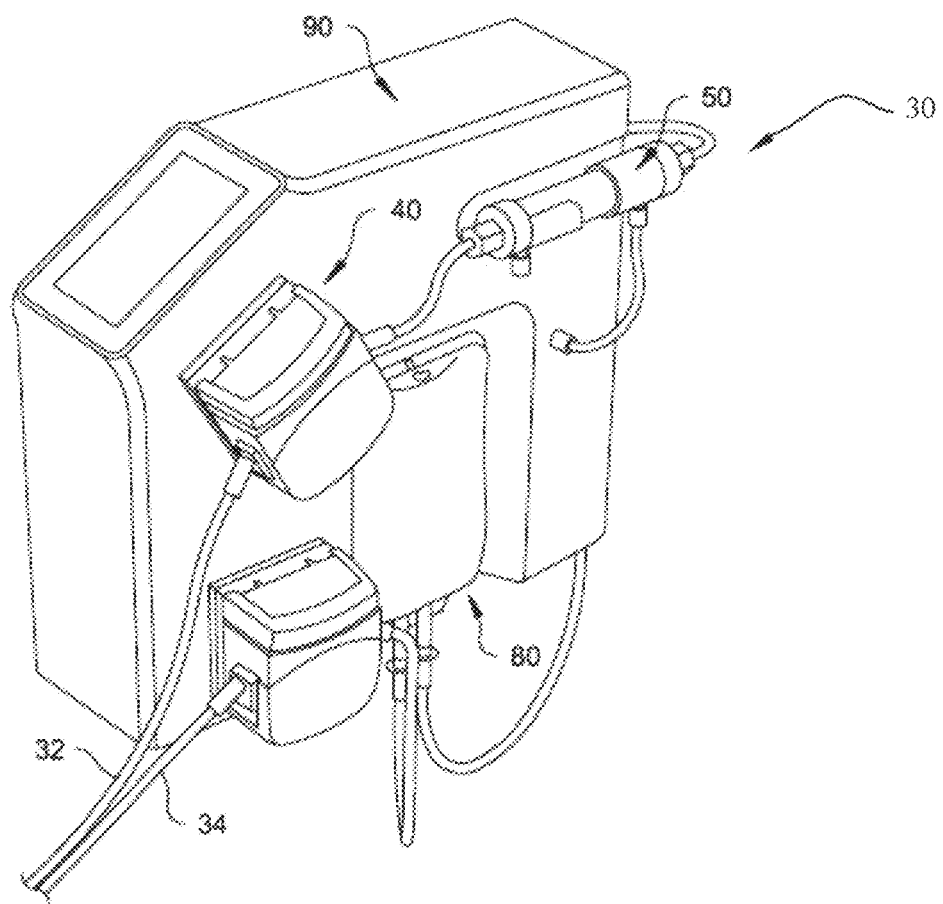
FIG. 2 is a perspective and magnified view of one embodiment of a fluid management system of the ultrasound system of FIG. 1A.
Figure 3:
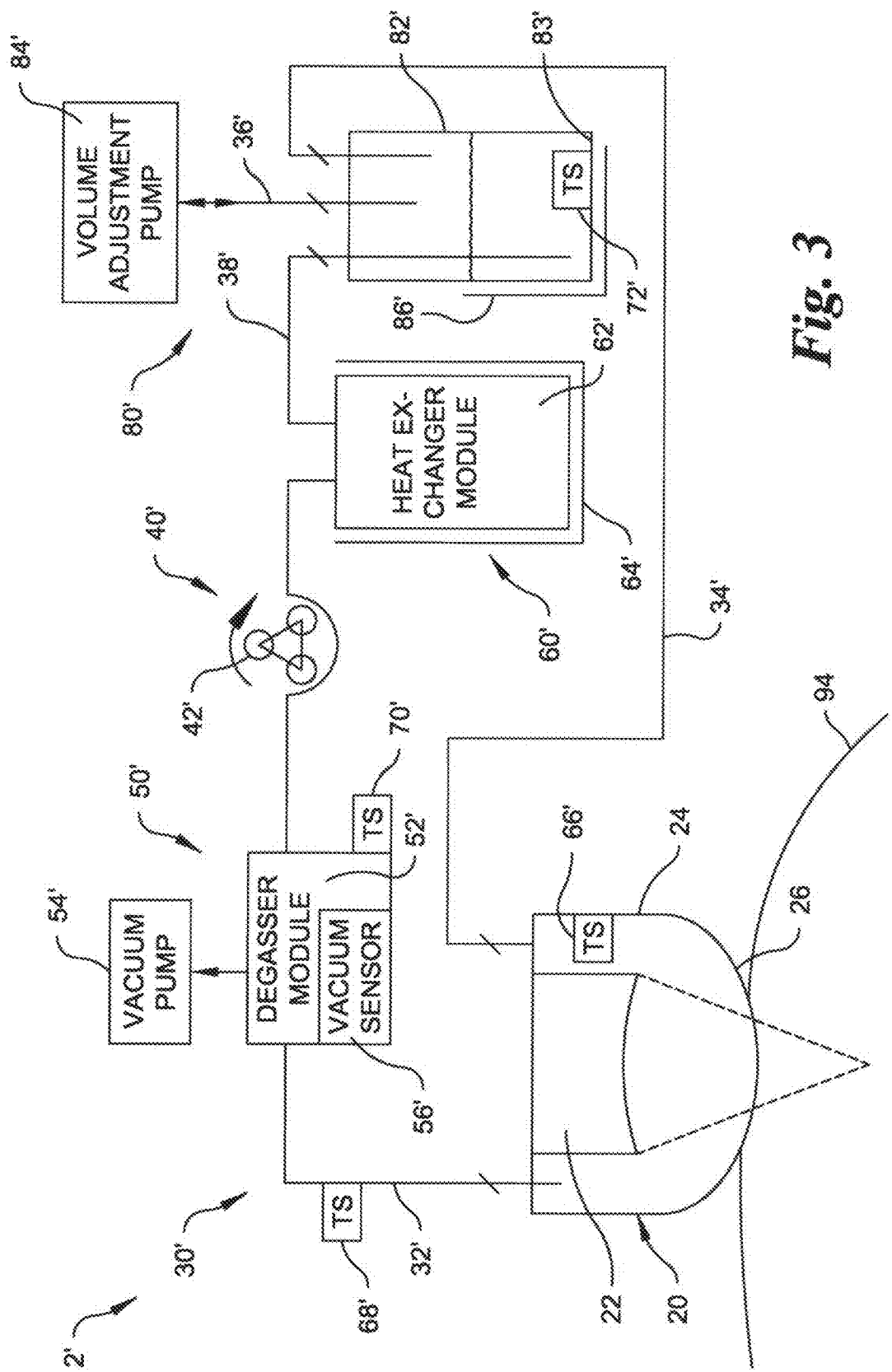
FIG. 3 is a simplified schematic view of the fluid management system according to one embodiment of the presently disclosed technology.
Figure 4:
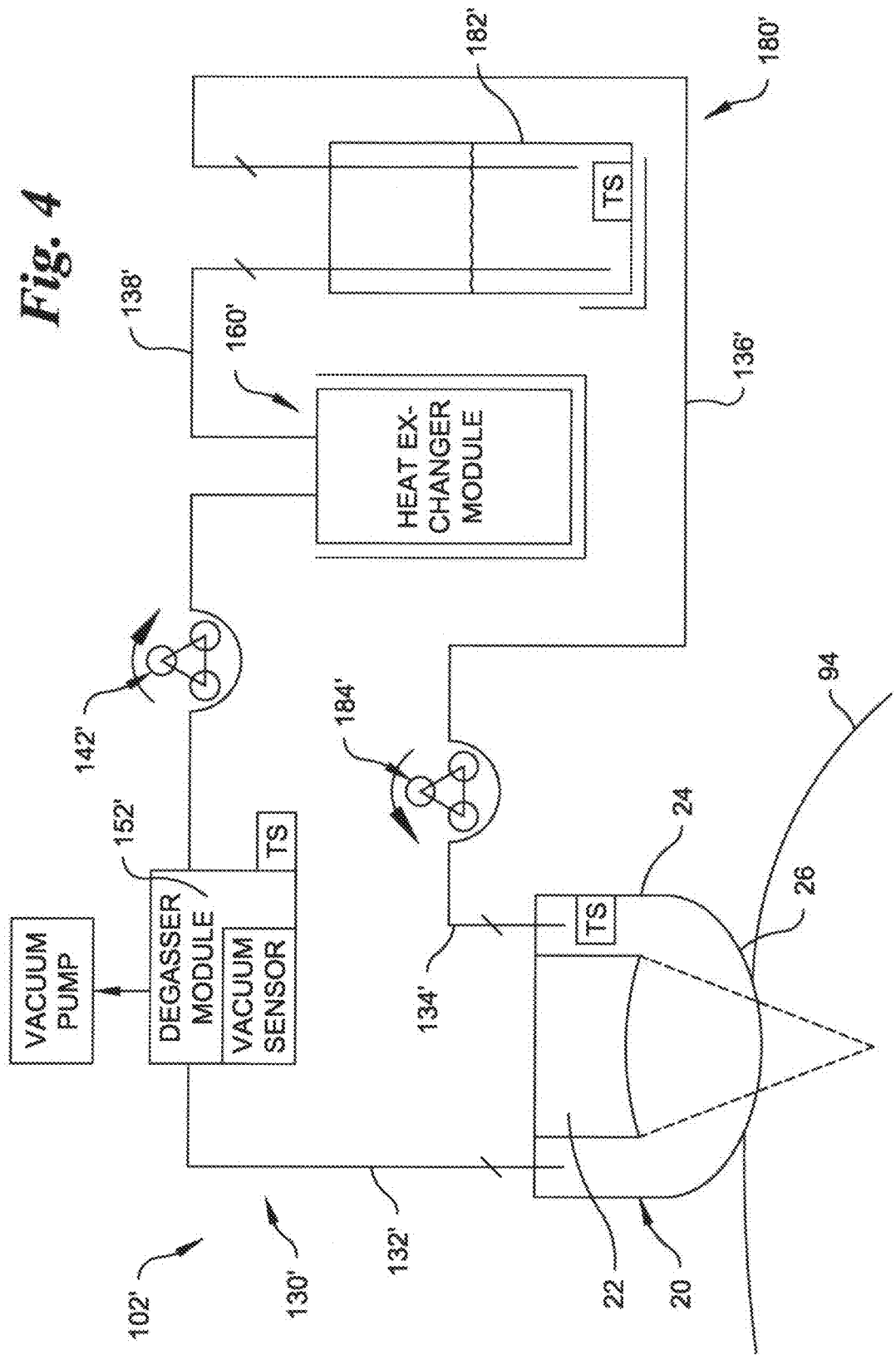
FIG. 4 is a simplified schematic view of another embodiment of the fluid management system.
Figure 5:
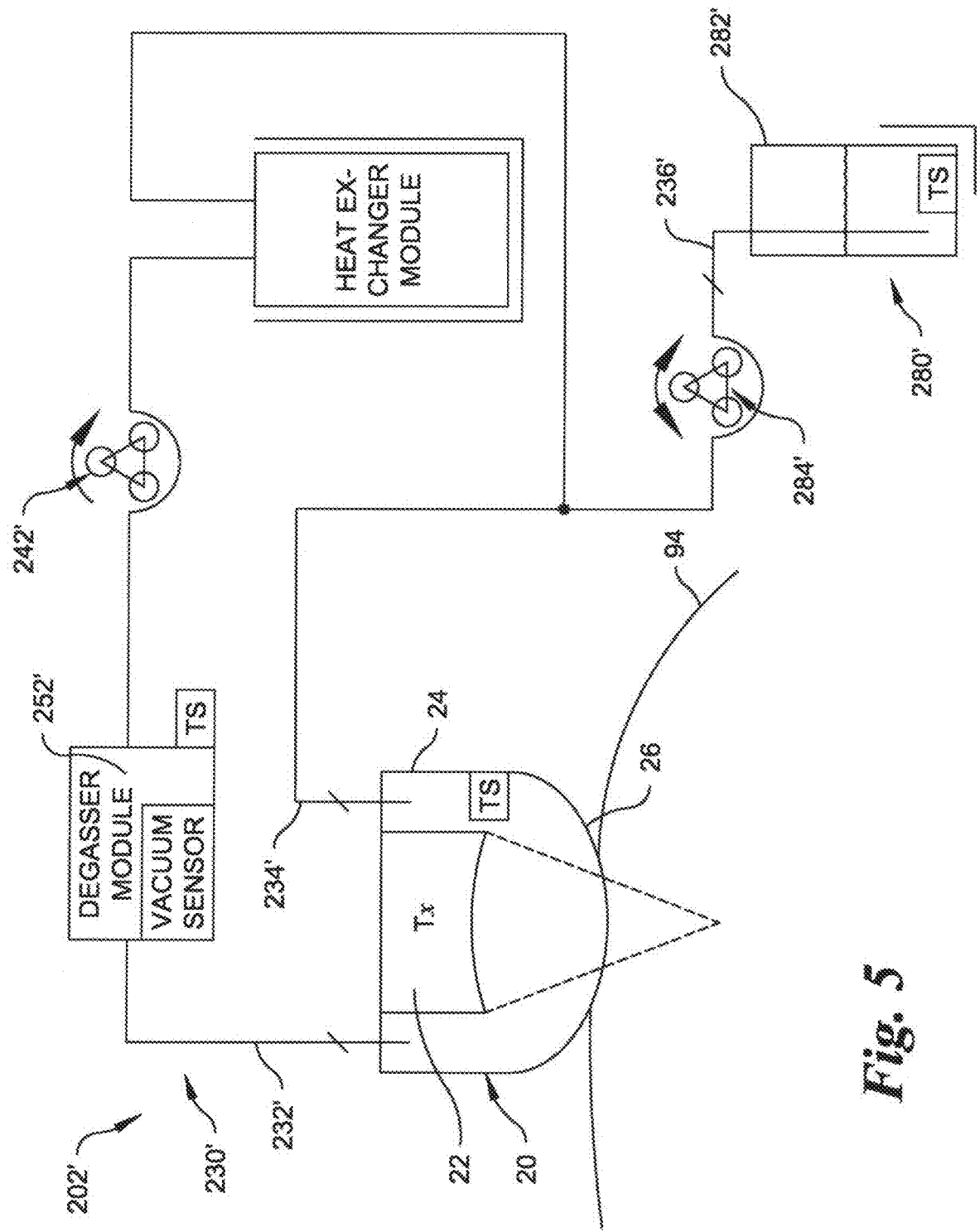
FIG. 5 is a simplified schematic view of yet another embodiment of the fluid management system.

FIGS. 1A and 1B show partially simplified and simplified schematic views, respectively, of an ultrasound system 2, 2' and therapeutic ultrasound coupling fluid management system 30 for the same in accordance with one embodiment of the presently disclosed technology. In the embodiment shown in FIG. 1B, the fluid management system can be housed or enclosed within a portion (e.g., a console 4') of the system 2'. FIG. 2 shows a magnified perspective view of the fluid management system 30 of FIG. 1A. FIGS. 3, 4 and 5 show simplified schematic views of three other fluid management systems 30', 130', 230' according to other non-limiting embodiments of the presently disclosed technology.

Referring specifically to FIG. 1A, the ultrasound system 2 is shown as employed with a console assembly 4. Optionally, the console assembly 4 can include, support or house a display or monitor 6, a keyboard or other input device 8, one or more wheels 10, and/or one or more computing devices (e.g., without limitation, one or more controllers or processors) of the fluid management system 30, as will be discussed below). The display 6 can include a touchscreen, a webcam, a speaker and a microphone, for example. The keyboard 8 can be a touchscreen and water-resistant, and can include a trackball or other control features.

The ultrasound system 2, 2' can include an ultrasound probe assembly 20, 20' (shown in simplified form in FIG. 1A, and a specific form of one embodiment in FIG. 1B) and the fluid management system 30, which is configured to be coupled to the probe assembly 20. The fluid management system 30 can be connected to the console, controlled by the console, or work in stand-alone mode, and can be configured to connect the console 4 to the probe assembly 20. In one embodiment, the fluid management system can be integrated into the console 4' (see, e.g., FIG. 1B). In another embodiment, the fluid management system 30 can be removably attachable to the console 4 and/or supported or held in place by an exterior surface of the console 4. In yet another embodiment, the fluid management system can be integrated into the probe assembly.

The ultrasound probe assembly 20 can include an ultrasound transducer assembly 22 and an ultrasound bolus assembly 24. The ultrasound bolus assembly 24 can be fixedly or removably coupled to the transducer assembly 22. The ultrasound bolus assembly 24 can include an acoustically transparent and distensible membrane 26 coupled to a window or opening of the ultrasound bolus assembly 24.

As shown in FIG. 2, the example fluid management system 30 can include a plurality of conduits (only two example conduits 32, 34 are shown in FIG. 2 for ease of illustration and economy of disclosure only), a fluid directing system 40, a fluid degassing system 50, a temperature control system (not visible in FIG. 2, but see, for example, temperature control system 60' shown schematically in FIG. 3), a volume adjustment system 80, and a housing 90 to support and/or contain at least some of the above-mentioned systems and/or other components. In one embodiment, the plurality of conduits can be removably attachable to each other and one or more of the systems mentioned above to form a single circuit fluid loop. In operation, the first and second conduits 32, 34 can be configured to extend from and be fluidly connected to a fluid inlet and a fluid outlet, respectively, of the probe assembly 20. Accordingly, in one embodiment, the first and second conduits 32, 34 provide locations where fluid can enter and exit, respectively, the ultrasound probe assembly 20. In one embodiment, the fluid inlet and outlets can be in the transducer assembly 22, and in another embodiment the fluid inlet and outlets can be in the bolus assembly 24.

In one embodiment, the fluid directing system 40 (see also fluid directing system 40' shown schematically in FIG. 3), the fluid degassing system 50 (see also fluid degassing system 50' shown schematically in FIG. 3), the temperature control system 60', the volume adjustment system 80 (see also volume adjustment system 80' shown schematically in FIG. 3), and the controller combine to provide significant improvements over the existing prior art. The order of each of these sub-systems within the (e.g., single) fluid loop is interchangeable or can be rearranged.

In one embodiment, the fluid directing system 40 can be located between a fluid inlet of the ultrasound probe assembly 20 (see FIGS. 1 and 2). In another embodiment, the fluid directing system 40' can be positioned between the fluid degassing system 50' and the temperature control system 60' (see FIG. 3). In certain circumstances, the latter arrangement can be preferred so that fluid passes through the fluid degassing system 50' as the last stage prior to reaching the patients, thereby reducing (or eliminating) the amount of gas and/or bubbles entering the ultrasound probe assembly 20.

Referring to FIG. 3, in one embodiment the fluid directing system 40' can include a first pump (e.g., without limitation, peristaltic circulation pump 42') fluidly connected to the first and second conduits 32', 34' in order to circulate fluid into and out of the probe assembly 20. In one example embodiment, fluid flow rates generated by the circulation pump 42' can range from 50-300 milliliters per minute. As such, the circulation pump 42' circulates fluid in the fluid path of the fluid management system 30' and can be employed to prime the probe assembly 20. The circulation pump 42' circulates fluid (e.g., without limitation, sterile water) without coming directly in contact with the fluid, thereby providing for a relatively sterile fluid loop. Accordingly, in the event that the membrane 26 becomes inadvertently detached from the bolus assembly 24, the likelihood that the fluid in the probe assembly 20 will comprise patient (e.g., see a portion of an example patient 94 in FIG. 3) safety will be significantly minimized. Furthermore, the circulation pump 42' can be selectively turned on or off, or have its direction reversed or have its circulation speed modulated or varied via an algorithm executed by the controller, which can include a custom printed circuit board (PCB) and a microcontroller.

Referring again to FIG. 3, the fluid degassing system 50', which is fluidly connected to the first and second conduits 32', 34', is configured to remove at least some gas from the fluid in the fluid management system 30' and/or the ultrasound probe assembly 20. As dissolved gases and/or gas bubbles within an ultrasound propagation path disrupt the ability of an ultrasound system to deliver energy to the target tissue of the patient, employing the fluid degassing system 50' advantageously improves the ability of the probe assembly 20 to deliver therapy to the patient 94. In one example embodiment, the fluid degassing system 50' includes one or more of a degasser module 52', a vacuum pump 54' coupled to the degasser module 52', and a vacuum sensor 56' coupled to the degasser module 52'. To maintain sterility, the degasser module 52' may be a single-use or disposable module. One example degasser module that may be employed as the degasser module 52' is FiberFlo Hydrophobic Capsule Filters, Part Number MV-C-030-K, of Valin Corporation, headquartered in San Jose, Calif. As shown, the degasser module 52' is fluidly and/or directly connected to the first conduit 32' and the circulation pump 42'. In operation, when the circulation pump 42' is circulating fluid in the fluid path (i.e., into and out of the degasser module 52'), the vacuum pump 54' is configured to draw gas out of the degasser module 52', thereby allowing fluid to be delivered to the probe assembly 20 relatively free of gas.

In one embodiment, the first conduit 32' can extend between the probe assembly 20 and the degasser module 52'. In one example embodiment, the circulation pump 42' is configured to circulate fluid in a counter-clockwise manner, with respect to the orientation of FIG. 3, such that fluid passes through the degasser module 52', into the first conduit 32', and then into the ultrasound probe assembly 20. While this configuration is only exemplary, the configuration can be advantageous in terms of delivering fluid into the ultrasound probe assembly 20 that contains relatively little gas, as opposed to alternative embodiments wherein fluid passes through other systems and/or components directly before being delivered to the probe assembly.

A vacuum level indicator can be used to monitor the vacuum level needed to remove all or some gas form the fluid management system 30'. In one example embodiment, vacuum levels generated by the vacuum pump 54' for effective fluid degassing range from approximately 25 to 29 inches of mercury. In one embodiment, this allows for degassing approximately one liter of water in under ten minutes. When the system or the user knows the pump(s) operating speed and the volume of fluid in the system, monitoring the vacuum and waiting a predetermined amount of time will remove at least a predetermined amount of gas from the system. In one embodiment, the fluid degassing system 50' is able to both remove dissolved gases from the fluid loop, as well as the gas contained in circulating gas bubbles. Optionally, the degasser module 52' is able to completely remove gas bubbles after a single pass of the gas bubble through the degasser module (e.g., the gas bubble enters on the one side of the module, but does not exit the other side). In certain circumstances, removing all dissolved gases may take more than one pass of the fluid volume though the degasser module 52'.

Similar to the circulation pump 42', the vacuum pump 54' may be selectively turned on or off manually and/or under algorithm control by the controller to degas fluid in the circulation loop until a desired value is reached (e.g., without limitation, less than or equal to three parts per million of dissolved $O_2$). More specifically, in one embodiment, the controller can be configured to measure vacuum levels in the degasser module 52' via the vacuum sensor 56', which may be a single use dissolved oxygen sensor to determine the dissolved gas content of the fluid in the fluid management system 30'.

The temperature control system 60' is fluidly connected to the first and second conduits 32', 34', and is configured to control the temperature of the fluid in the ultrasound probe assembly 20. The example temperature control system 60' in the embodiment shown in FIG. 3 includes a heat exchanger module 62', a heating (and/or cooling) element 64' coupled to the heat exchanger module 62', and a plurality of spaced-apart temperature sensors (four example, temperature sensors 66', 68', 70', 72' are shown in FIG. 3). In one embodiment, the temperature control system can include a single-use/disposable aluminum block 62' with serpentine tubings inside to maximize heat transfer area, tightly (but removably) coupled to thermoelectric elements (e.g., Peltier junction devices, also known as TECs).

In one embodiment, the heat exchanger module 62' is fluidly coupled to the circulation pump 42', the degasser module 52', the first and second conduits 32', 34', the ultrasound probe assembly 20, and the volume adjustment system 80'. As shown, in one embodiment, the heating and/or cooling element 64' is coupled to the heat exchanger module 62' such that heat can be added or subtracted to the circulation fluid without coming in direct contact with the fluid. This provides advantages in that the fluid can remain relatively sterile, thereby protecting the patient 94. Furthermore, by being coupled to the heat exchanger module 62', maximum heat flow is advantageously able to be achieved. Coupling the heat exchanger module 62' to the heating and/or cooling element 64' is preferentially performed by using thermal conductive pads mounted on all sides of 62' (such as those manufactured by T-global Technology, H48-6 Thermal Conductive Pad, 0.5 mm thick, or similar). Less thermally efficient coupling of the heat exchanger module 62' to the heating/cooling element 64' may also be performed by filling the cavity of the heating/cooling element 64' with a thermally conductive fluid (i.e., water).

Example heating and/or cooling elements that may be employed as the heating and/or cooling element 64' include, but not limited to, one or more thermoelectric elements, resistive heating elements, and refrigeration systems. As shown, one of the temperature sensors 66' is directly connected with and/or attached to the bolus assembly 24. One or more similar suitable alternative temperature sensors may be coupled to the heating and/or cooling element 64' (to measure its performance), the transducer assembly 22 instead of or in addition to being coupled to the bolus assembly 24. In one embodiment, three of the temperature sensors 68', 70', 72' are each coupled to one of the plurality of conduits 32', 34', the fluid degassing system 50', and the volume adjustment system 80'. While the fluid management system 30' is described herein in association with the four temperature sensors 66', 68', 70', 72', it will be appreciated that a similar suitable alternative fluid management system may have any number of temperature sensors.

Depending upon the circumstances and/or the particular arrangement, the temperature sensor 66' is the most important one from an operation perspective, as the temperature in the probe assembly is the most important temperature in the fluid loop that needs to be controlled/managed. Thus, in one embodiment, the function of most other temperature sensors in and around the loop are mostly for control and/or system performance monitoring functions.

In one embodiment, the temperature sensors 66', 68', 70', 72' each cooperate with the heat exchanger module 62' to control temperature of the fluid in the ultrasound probe assembly 20. In one example embodiment, the fluid management system 30 can include a number of cables (not shown) to connect the temperature sensors 66', 68', 70', 72' to one of the controller or the console assembly 4 (FIG. 1A) via Ethernet connections. Alternatively, the temperature sensors 66', 68', 70', 72' can be wirelessly connected to one of the controller or the console assembly 4 (FIG. 1A). Furthermore, the controller can be configured to measure the temperature of the heat exchanger module 62'.

In one example embodiment, the controller employs an algorithm to control the temperature control system 60'. Specifically, one or more of the temperature sensors 66', 68', 70', 72' can relay data of the temperature of the circulating fluid in the ultrasound system 2, 2' to the controller, which, by way of algorithm control, cooperates with the heating and/or cooling element 64' to raise or lower the temperature of the circulating fluid. In one implementation, the temperature control system 60' continuously cools the fluid, which in turn cools the transducer assembly 22, and thus cools the tissue of the patient 94 in contact with the probe assembly 20. This provides beneficial protection to the probe assembly 20 against overheating. In another implementation, the temperature control system 60' maintains the fluid at a set temperature that may be perceived as comfortable and safe for coming into contact with the patient 94. This may increase patient comfort and safety when the membrane 26 engages the skin of the patient 94. For example, the operating temperature setpoint may be defined by a user or may be set automatically based on a given use. The operating temperature setpoint may also be increased or decreased, as needed.

In one embodiment, the volume adjustment system 80' is fluidly connected to the first and second conduits 32', 34', and is configured to adjust the volume of the fluid in the ultrasound probe assembly 20. This is beneficial because it allows operating personnel to control the distance between the transducer assembly 22 and the patient 94. As such, the single transducer assembly 22 may be employed to target tissue at different depths.

The volume adjustment system 80' can include a fluid reservoir 82' (e.g., without limitation, semi-rigid 500 milliliter or 1000 milliliter reservoir, deformable bag, or pouch containing at least some sterile water), a second pump 84' (e.g., without limitation, volume adjustment pump) fluidly connected to the reservoir 82', and a weight measurement system 86' coupled to the reservoir 82'. The weight measurement system 86' can be configured to measure the weight of the fluid in the reservoir 82' and cooperate with the controller in order to control the addition or subtraction of gas into the reservoir 82'. As shown, in one embodiment, the second conduit 34' extends between the ultrasound probe assembly 20 and the reservoir 82'. The plurality of conduits of the fluid management system 30' can further include a third conduit 36' extending between the reservoir 82' and the volume adjustment pump 84'. In operation of one embodiment, the volume adjustment pump 84' is a gas pump that is configured to inject gas into and remove gas from the reservoir 82' to thereby add fluid into and/or remove fluid from the ultrasound probe assembly 20, respectively. Because the ultrasound probe assembly 20 is the only deformable member of the fluid path (i.e., by virtue of the distensible membrane 26), fluid will either be added or removed from this part of the fluid path, effectively increasing the distance between the transducer assembly 22 and the target tissue (when fluid is added), or decreasing the distance between the transducer assembly 22 and the target tissue (when fluid is removed).

Thus, in one embodiment, the reservoir 82' can include three ports or openings (e.g., and can include a three port cap). In particular, the reservoir 82' can include one port for the volume adjustment pump 84', and two ports for addition and removal of fluid from the reservoir 82'. In one example embodiment, as described below the volume adjustment system 80' is also configured to at least substantially avoid adding gas bubbles into the fluid path. The reservoir 82' can have a bottom portion or surface 83'. The third conduit 36' can have a distal end spaced-apart a first distance from the bottom portion 83'. The second conduit 34' can have a distal end spaced-apart a second distance from the bottom portion 83'. The second distance can be less than the first distance. In one embodiment, as shown in FIG. 3, the plurality of conduits of the fluid management system 30' can include a fourth conduit 38'. The fourth conduit 38' can provide an outlet for fluid to exit the reservoir 82'. The fourth conduit 38' can have a distal end located proximate the bottom portion 83' of the reservoir 82', such that the distal ends of the second and third conduits 34', 36' are spaced-apart greater distances from the bottom portion 83'. In this manner, fluid will generally only be drawn from the bottom of the reservoir, thereby minimizing the likelihood that gas will enter the fluid path.

The volume adjustment system can employ a deformable bladder member within or instead of the reservoir described above. In such an implementation of the disclosed technology, the bladder member may be inflated or deflated by an air pump in order to achieve volume control by displacing fluid out of and into the reservoir. A particular advantage of this implementation is that fluid will not be exposed to ambient air.

To control the volume adjustment system 80', in one example embodiment, the controller employs an algorithm to automatically control the volume of the fluid in the ultrasound probe assembly 20 so that the distance between the transducer assembly 22 and the target tissue is the desired distance for the treatment. In another example embodiment, the volume of the fluid in the ultrasound probe assembly 20 can be adjusted manually.

As a result of the above-described systems, structure and function, the fluid management system 30' can operate as a single unit configured to provide multiple advantages for delivering ultrasound therapy. Specifically, the fluid management system 30' is advantageously able to introduce fluid into the ultrasound probe assembly 20 that is relatively free of bubbles and/or gas (i.e., via or because of the fluid degassing system 50'). The fluid management system 30' is also able to control the temperature of the fluid in the ultrasound probe assembly 20 (i.e., via or because of the temperature control system 60'). Finally, the fluid management system 30' is able to control the volume of the fluid in the probe assembly 20 (i.e., via or because of the volume adjustment system 80'). As discussed, these functions may optionally all be performed manually, or automatically under algorithm control by the controller.

While the instant embodiment of the presently disclosed technology has been disclosed in association with fluid flowing out of the ultrasound probe assembly 20, into and out of the reservoir 82', into and out of the heat exchanger module 62', past and/or through the circulation pump 42', through the degasser module 52', and into a fluid inlet of the ultrasound probe assembly 20, the instant configuration is exemplary only, and is not meant to be a limiting aspect of the disclosed technology. However, if temperature control within the ultrasound probe assembly 20 is a primary concern, it may be prudent to place a temperature control system closest to a transducer assembly in an alternative fluid management system in order to minimize heat loss. If the gas content of the fluid in the ultrasound probe assembly is of highest concern, as is the case in the fluid management system 30', it may be prudent to place a degasser module closest to a transducer assembly to minimize the dissolved gas content of the fluid reaching the ultrasound probe assembly 20. For example, in FIG. 3, fluid is configured to circulate counterclockwise, and the degasser module 52' is positioned between the ultrasound probe assembly 20 and the circulation pump 42', the heat exchanger module 62', and the reservoir 82'.

As described in detail below, in one embodiment the fluid management system 30' employs or works in conjunction with a single-loop, disposable fluid path, which is relatively simple to set up by a user. Specifically, in one embodiment, there can be five touch or connection points in which the fluid path interfaces to the fluid management system 30' and/or is separable: First, the connection of the degasser module 52'; Second, the placement of the conduits in the circulation pump 42'; Third, the placement of the heat exchanger module 62' in the fluid path; Fourth, connecting the reservoir 82' to the fluid path; Fifth, the two connection points to the fluid inlet and the fluid outlet of the ultrasound probe assembly 20. In one embodiment, it can be beneficial to maintain these user touch points to a minimum to facilitate initial setup. By employing a single-loop fluid path with the inline components described herein (e.g., without limitation, degasser module 52', heat exchanger module 62', and cap for the reservoir 82'), a relatively sterile implementation and use of this system is advantageously able to be achieved. Furthermore, the integrity of the fluid is maintained in this closed-loop system, and all parts of the fluid path can be sterilized in advance.

Because substantially all of the functions of the fluid management system 30' are able to be controlled under algorithm via the controller, several tasks that previously required significant user intervention can now be automated. These tasks include system priming, system debubbling, verifying dissolved gas content of the circulating fluid, and/or volume control of the probe assembly 20.

The following is a description of one method of priming the system 30'. Initially, the user can connect the probe assembly 20 and the reservoir 82' to the fluid path, and place the heat exchanger module 62' in the system 30' and/or the plurality of conduits. The fluid management system 30' can automatically be primed and the conduits/fluid path and the probe assembly 20 can be filled by activating the circulation pump 42'. The weight/volume of the remaining fluid in the reservoir 82' can be monitored. In one embodiment, the controller would know or be pre-programmed with how much fluid is required to prime/fill the fluid path and probe assembly 20 for the first time, and can activate the circulation pump 42' until this weight or volume has been released to fill the path and probe assembly 20. At the same time, the air volume and pressure in the reservoir 82' can be monitored by the fluid management system 30'. Air and/or pressure can be added and/or removed as necessary in order to achieve a steady state for the fluid volume in the probe assembly 20. The fluid management system 30' could then alert the user once the priming operation is completed.

The following is a description of one method of debubbling and verifying the dissolved gas content in the system 30'. Debubbling requires gas bubbles located in the probe assembly 20 to be removed or kept below a predetermined level or amount, so that the gas will not interfere with the transmission of ultrasound energy from the transducer assembly 22 through the fluid to the target tissue. This may be accomplished by the proposed fluid management system 30', wherein the controller could be configured to determine the amount of fluid required to completely fill the probe assembly 20 without gas pockets, and instruct the user to tap or shake the probe assembly 20 to remove all trapped gas bubbles from the probe assembly 20 until they are transferred to the reservoir 82'. In addition, because of the presence of the vacuum sensor 56', the fluid management system 30' could automatically alert the user once the fluid in the fluid path has achieved the desired level of dissolved gases, indicating that the system is ready to be used in the ultrasound therapeutic procedure.

In one embodiment, whether or not the desired volume of fluid in the probe assembly 20 has been achieved will primarily be determined by measuring the distance between the transducer assembly 20 and the target tissue (e.g., without limitation, by using either ultrasound imaging or pulse-echo ranging techniques), and not by the fluid volume in the probe assembly 20 or remaining fluid volume in the reservoir 82'. A weight and/or volume measurement would not be sufficient because of the deformable nature of the probe assembly 20 (e.g., via the flexible membrane 26), as many different volumes in the probe assembly 20 would lead to similar distances between the transducer assembly 22 and target tissue, mostly because of how and with what force the user would place the probe assembly 20 on the patient.

A weight and/or volume measurement would, however, generate a first 'guess' for this distance because of known parameters of the system (e.g., total fluid volume, priming volume, pressure of the air in the reservoir, probe assembly size, typical bolus distention, etc.). If more separation between the transducer assembly 22 and the target tissue is required or desired based on the ultrasound imaging data, a command could be sent (e.g., from the controller to a pump) to increase the volume of fluid in the reservoir 82'. The fluid management system 30' would issue the appropriate local commands to its various components (e.g., activate the volume adjustment pump 84' to increase the air volume in the reservoir 82'). In one embodiment, an algorithm for the controller can be based on the change of volume in the reservoir 82' over time ($\Delta V/\Delta t$) in order to control the probe assembly 20 filling/emptying and steady state behavior, preferably maintaining $\Delta V/\Delta t=0$ during steady state, targeting a large $\Delta V/\Delta t$ during the beginning of the filling and emptying procedure, gradually targeting a smaller $\Delta V/\Delta t$ towards the end of the filling and emptying procedure to avoid volume over/undershoot, but still obtain a fast system response to the filling/emptying request.

The sensors of the fluid management system 30' (e.g., without limitation, one or more of the vacuum sensor 56' and the temperature sensors 66', 68', 70', 72') can be used to (i) verify the correct functioning of the fluid management system 30', and/or (ii) stop the operation of the fluid management system 30' if a malfunction (either system or user-generated) is detected. One example is (i) undesired fluid accumulation in the probe assembly 20 because of a pinched fluid return path, (ii) insufficient cooling performance because of incorrect connection of the heat exchanger module 62' by the user, (iii) compromised degassing performance due to the degasser module 52' malfunctioning, and/or (iv) the presence of a leak in the fluid management system 30'. In one embodiment, to maintain sterility and to keep costs low, one or more of the sensors would be in contact with the outside of the components of the system 30'. In certain embodiments, interior or in-line sensors can unnecessarily or undesirably increase cost and complexity. Non-contact sensors (IR-based) are preferred in at least some embodiments.

While the fluid management system 30' has been described thus far in association with the therapeutic ultrasound system 2', the fluid management system 30', or a similar suitable alternative fluid management system (e.g., without limitation, fluid management systems 130', 230', shown in FIGS. 4 and 5, respectively) may be employed with any therapeutic ultrasound system (e.g., without limitation, a system utilizing HIFU, hyperthermia, or non-ablative ultrasound, etc., utilizing either extracorporeal ultrasound applicators, intracorporeal applicators, or intracavity ultrasound applicators) and/or a diagnostic ultrasound system.

Referring to FIG. 4, another embodiment of the fluid management system 130' will now be discussed in detail. The fluid management system 130' shown schematically in FIG. 4 functions similar to, and includes similar components as, the fluid management system 30', discussed above. As such, like reference numerals will be used to represent like components. Furthermore, for ease of illustration and economy of disclosure, and unless otherwise stated, only significant differences between the fluid management systems 30' and the fluid management systems 130' will be discussed in detail.

The volume adjustment system 180' of the fluid management system 130' can include a fluid reservoir (e.g., without limitation, deformable bladder member 182') and a second pump in the form of a peristaltic circulation pump 184'. Similar to the fluid management system 30' of the first embodiment (FIG. 3), the first conduit 132' extends between the probe assembly 20 and the degasser module 152'. However, in contrast to the first embodiment, the second conduit 134' of the second embodiment extends between the probe assembly 20 and the second circulation pump 184'. Furthermore, the plurality of conduits of the fluid management system 130' further includes a third conduit 136' extending between the bladder member 182' and the second circulation pump 184'.

In operation of one embodiment, the first and second pumps 142', 184' can cooperate to increase/decrease the fluid volume in the probe assembly 20. Specifically, by modulating the speed of the first and second pumps 142', 184', the fluid volume in the probe assembly 20 can be controlled, such as described in U.S. Patent Application Publication No. 2016/0236013. In the fluid management system 130' of one embodiment of the presently disclosed technology, both of the first and second pumps 142', 184' function as circulating pumps to circulate fluid. Accordingly, in order to adjust the volume of the fluid in the probe assembly 20, the first and second pumps 142', 184' run at different speeds. Once the fluid volume in the probe assembly 20 is set, the first and second pumps 142', 184' are configured to run at the same speed.

Referring again to FIG. 4, the plurality of conduits further includes a fourth conduit 138' extending from the bladder member 182' to the heat exchanger module 160'. The third and fourth conduits 136', 138' each have a distal end located proximate a bottom portion of the bladder member 182'. This is advantageous in that fluid flowing into and out of the bladder member 182' will generally not result in the addition of gas bubbles into the circulation path.

Referring to FIG. 5, yet another embodiment of the fluid management system 230' will now be discussed in detail. The fluid management system 230' functions similar to, and includes similar components as, the embodiments of the fluid management systems 30', 130' discussed above. As such, like reference numerals will be used to represent like components. Furthermore, for ease of illustration and economy of disclosure, and unless otherwise stated, only significant differences between the fluid management systems 30', 130' and the fluid management system 230' will be discussed in detail.

As shown, the volume adjustment system 280' of the fluid management system 230' includes a fluid reservoir (e.g., without limitation, deformable bladder member 282'), a first pump 242' (e.g., a circulation pump) and a second pump 284' (e.g., a volume adjustment pump), both of which can be in the form of a peristaltic circulation pump. The second pump can form part of the volume adjustment system 280', or the second pump can be a separate component from those of the volume adjustment system 280'. Similar to the earlier-described embodiment of the fluid management system 30' (FIG. 3), the first conduit 232' extends between and fluidly connects the fluid inlet of the probe assembly 20 and the degasser module 252'. The second conduit 234' fluidly connects the fluid outlet of the probe assembly 20 to the second circulation pump 284'. Furthermore, the plurality of conduits of the fluid management system 230' includes a third conduit 236' extending between and fluidly connecting the bladder member 282' to the second circulation pump 284'. As shown, the third conduit 236' can fluidly connect to the second conduit 234' by way of a T-junction. In contrast to the above-described embodiments, the present embodiment can include only a single fluid connection (i.e., the third conduit 236') to the bladder member 282'.

In operation, the fluid management system 230' can employ or operate the first pump 242' to circulate fluid constantly, and only activate the second pump 284' (e.g., selectively running the second pump 284' clockwise and/or counterclockwise) to add and/or remove fluid from the bladder member 282', thereby allowing the volume of the fluid in the probe assembly 20 to be adjusted. For example, to add fluid to the probe assembly 20, the first pump 242' can operate normally and the second pump 284' can turn clockwise until the scale registers or senses a decrease in weight of the reservoir. This may be accomplished by a user activating a button and/or a touchscreen (e.g., on the housing 90), or the system can receive an "add volume" command to add fluid to the probe assembly 20. To remove fluid in one embodiment, the first pump 242' can run normally, the second pump 284' can turn or rotate counterclockwise until the scale registers or senses and increase in weight of the reservoir. The second pump 284' can then at least temporarily cease operation.

To control the fluid volume addition or removal, the number of revolutions of second pump 284' and the known-diameter third conduit 236' could be used for volume control instead of relying on the removal or addition of fluid/weight from the reservoir 282'. This open-loop-control of fluid volume in the probe assembly 20 may not be as accurate as the closed-loop-control of fluid volume that relies on weight feedback from the weight measurement system 86', but this open-loop-control is less susceptible to weight measurement errors from the weight measurement system, which occur, for example, when the bladder member 82' is accidentally manipulated (or bumped into) during the volume adjustment operation.

Operation of one embodiment can be completed as follows: use open-loop-control of volume addition/removal from the probe assembly 20 during volume addition/removal steps by actuating the second pump 284' as per the fixed ml/rev value (weight measurement system is not interrogated for a weight during this step), and after completion, interrogate the weight measurement system 86' to verify (within a margin of error) if the correct fluid volume was added/removed from the bladder member 282'. This provides sufficient operation for volume control, and minimizes error indications from the weight measurement system 86' due to vibration, noise, and/or accidental user manipulation of the bladder member 282'. This is possible as the actual value of the volume added or removed from the probe assembly 20 is not the deciding factor, but what separation it generates between the transducer assembly 22 and the patient 94.

One method of priming an probe assembly 20 with a fluid management system 30', 130', 230' can include the steps of providing the fluid management system 30', 130', 230', providing the volume adjustment system 80', 180', 280' with a fluid reservoir 82', 182', 282' and a pump 84', 184', 284' fluidly connected with the fluid reservoir 82', 182', 282', and activating the pump 84', 184', 284' in order to add fluid into or remove fluid from the ultrasound probe assembly 20, respectively. The activating step can further include activating the pump 184', 284' such that fluid flows in a clockwise direction through the pump 184', 284', and at least one method can further include a step of activating the circulation pump 142', 242' such that fluid flows in a counterclockwise direction through the circulation pump 142', 242'.

In one embodiment, the system can be primed by operating both pumps 242', 284' to turn clockwise until the scale registers or senses a decrease in weight of the reservoir. Once the required volume and/or weight has been removed from the reservoir (e.g., as measured by the scale), the second pump 284' at least temporarily ceases operation while the first pump 242' continues to operate. In one embodiment, the system and/or fluid loop can be purged by employing the same process as described above for priming, but in reverse (e.g., operating the pumps 242', 284' counterclockwise).

The fluid management system 230' of the present embodiment provides substantially the same advantages as the fluid managements systems 30', 130' of the earlier-described embodiments, as well as additional advantages. For example and without limitation, the second circulation pump 284' is only configured to operate when fluid is added and removed from the fluid loop. Otherwise, the second circulation pump 284' is configured to stay in an off condition, thus reducing power consumption and/or noise. Additionally, users only need to make one single connection (e.g., the third conduit 236') to the bladder member 282', thereby simplifying assembly. Further, a more accurate weight can be determined by a scale connected to the bladder member 282', as vibration from pumps and system noise is reduced, which allow for better and/or more accurate volume control.

By operating one or more of the pumps 42', 84', 142', 184', 242', 284', various values, such as flow rate, can be measured and/or quantified during the initial system test (e.g., by measuring how quickly the pumps 84', 184', 284' can add or subtract water from the reservoirs 82', 182', 282'). This parameter can be used for a system pass/fail test, and/or used in subsequent calculations for determining degassing performance, cooling performance, etc. By operating the pumps 42', 142', 184', 242', 284' one at a time or in series, and varying their pumping direction prior to fully priming the system, the system will be able to (i) determine if the user has either placed the conduits of the fluid path in the correct orientation within the peristaltic pumps 42', 142', 184', 242', 284', (ii) inform the user to change the orientation/direction of the conduits of the fluid path if set up incorrectly, and/or (iii) take the orientation/conduit placement into account automatically when operating the system, so as to be able to compensate for incorrectly oriented conduit direction by the user, by simply reversing the pumping direction of the peristaltic pumps 42', 142', 184', 242', 284'. By at least briefly or temporarily rotating the pumps 42', 84', 142', 184', 242', 284' in either way, one at a time, and monitoring the addition (or removal) of fluid in the reservoirs 82', 182', 282' via the weight measurement systems (only one of the three weight measurement systems 86' is shown in the drawings), the system would be able to accomplish this function.

2. Embodiments of Single Fluid Loop

Figure 6:
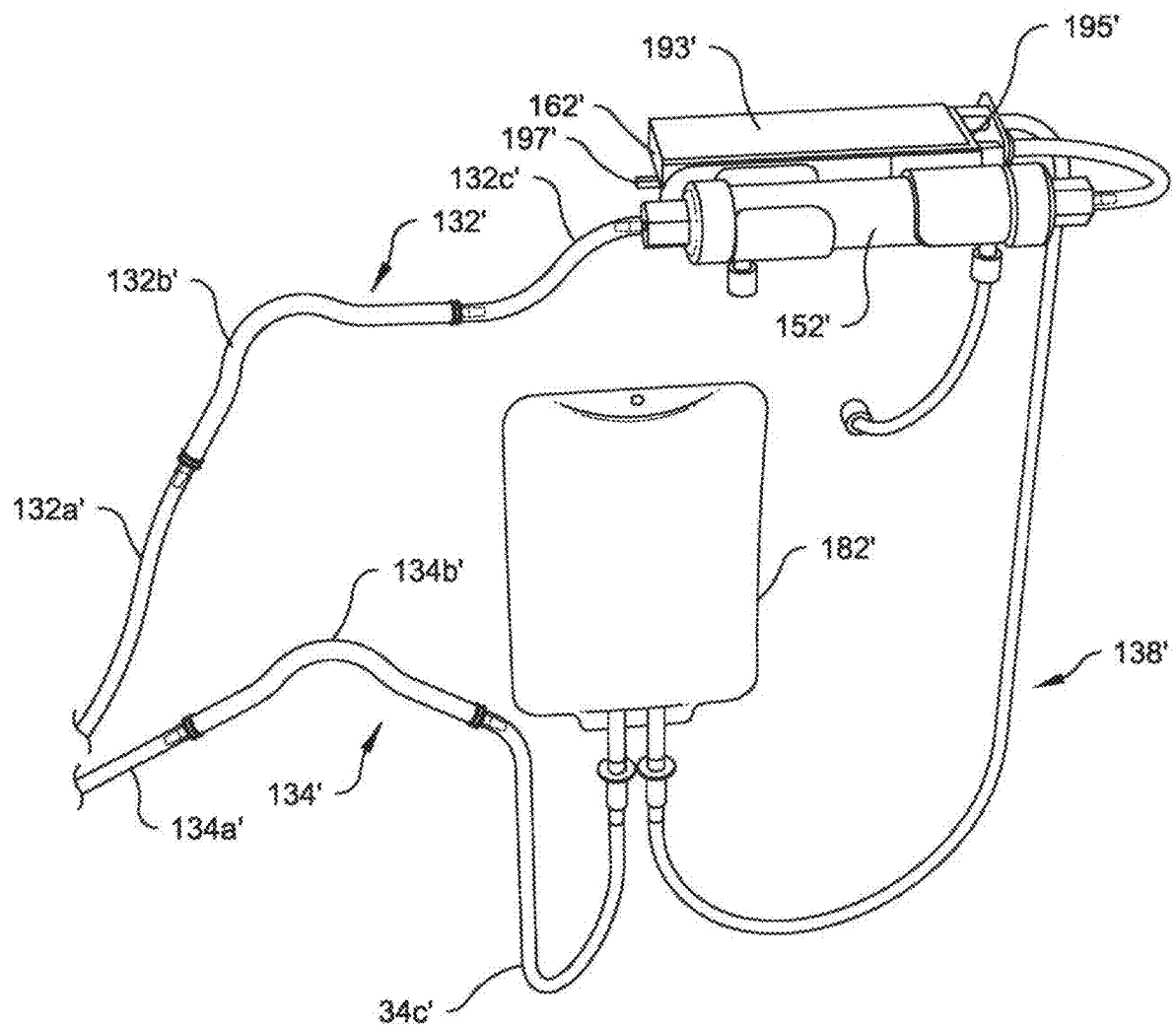
FIG. 6 is a perspective view of certain components of one embodiment of the fluid management system of the presently disclosed technology.
Figure 7:
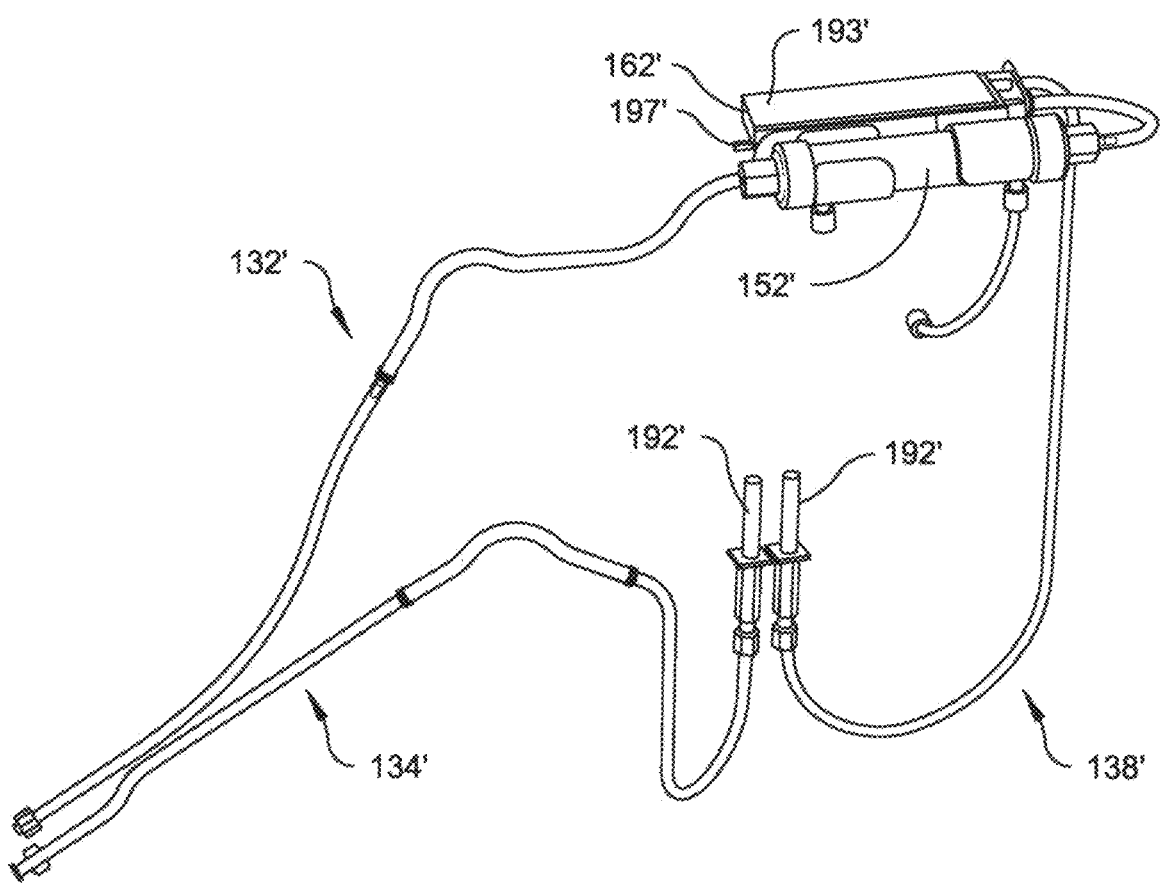
FIG. 7 is another perspective view of certain components of one embodiment of the fluid management system of the presently disclosed technology.
Figure 8:
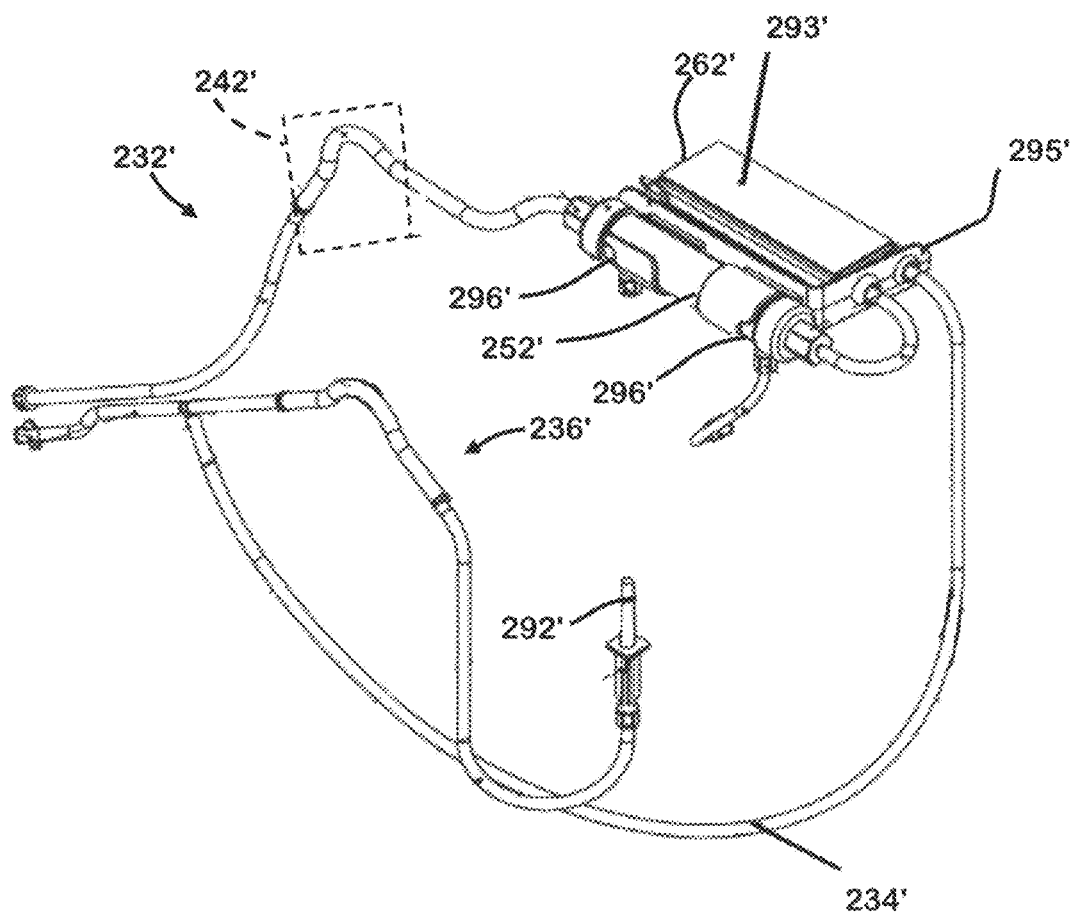
FIG. 8 is yet another perspective view of certain components of one embodiment of the fluid management system of the presently disclosed technology.
Figure 9:
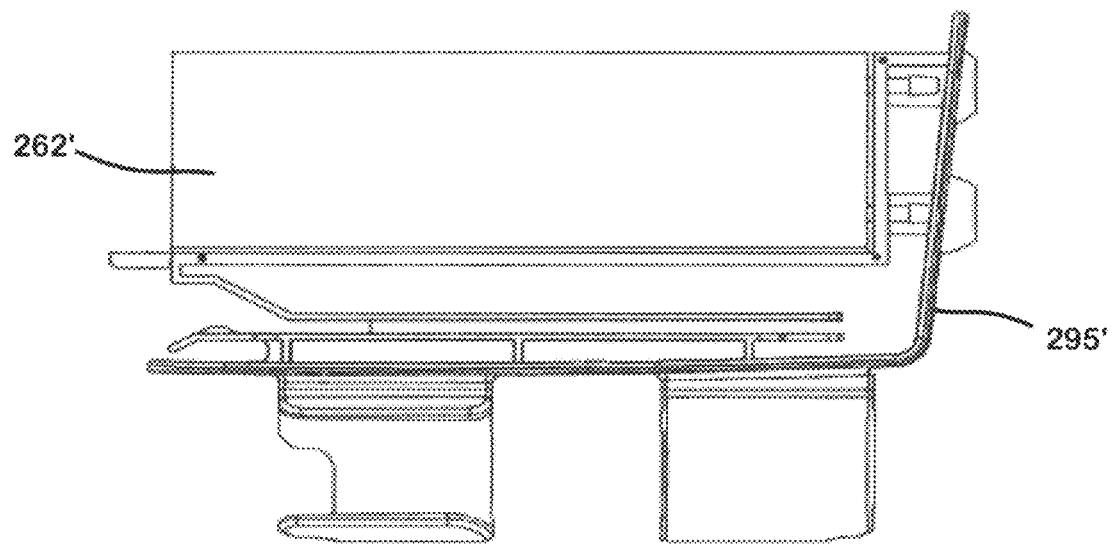
FIG. 9 is a side elevation view of at least a portion of the fluid management systems shown in FIGS. 6-8.
Figure 10:
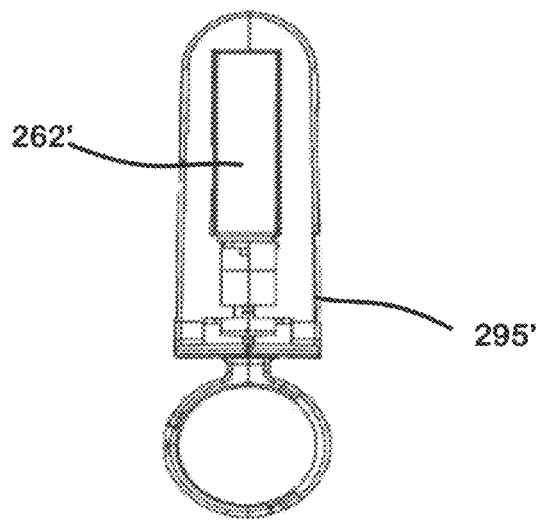
FIG. 10 is another side elevation view of the components shown in FIG. 9.

Referring specifically to the different embodiments shown in FIGS. 6-8, as mentioned above, the presently disclosed technology includes a plurality of conduits that can be removably attachable or separable conduits that, when combined with the probe assembly 20, for a single fluid circuit or loop. In one embodiment, the plurality of conduits can form a portion of the fluid management system 30, 130', 230', and can be removably or permanently attachable to one or more of the components of the fluid management systems 30, 130', 230' described above. Alternatively or additionally, one or more of those components can be positioned within the single fluid circuit or directly attached to one of the individual conduits of the plurality of conduits.

The single fluid circuit can include three, four or more separate conduits. For example, as shown in FIG. 8, three separate conduits can be fluidly connected by the probe assembly, the degasser module 252', and the heat exchanger module 262'. Another example, as shown in FIGS. 6 and 7, four separate conduits can be fluidly connected by the probe assembly, the degasser module 152', the heat exchange module 162 and the reservoir 180'.

Figure 11:
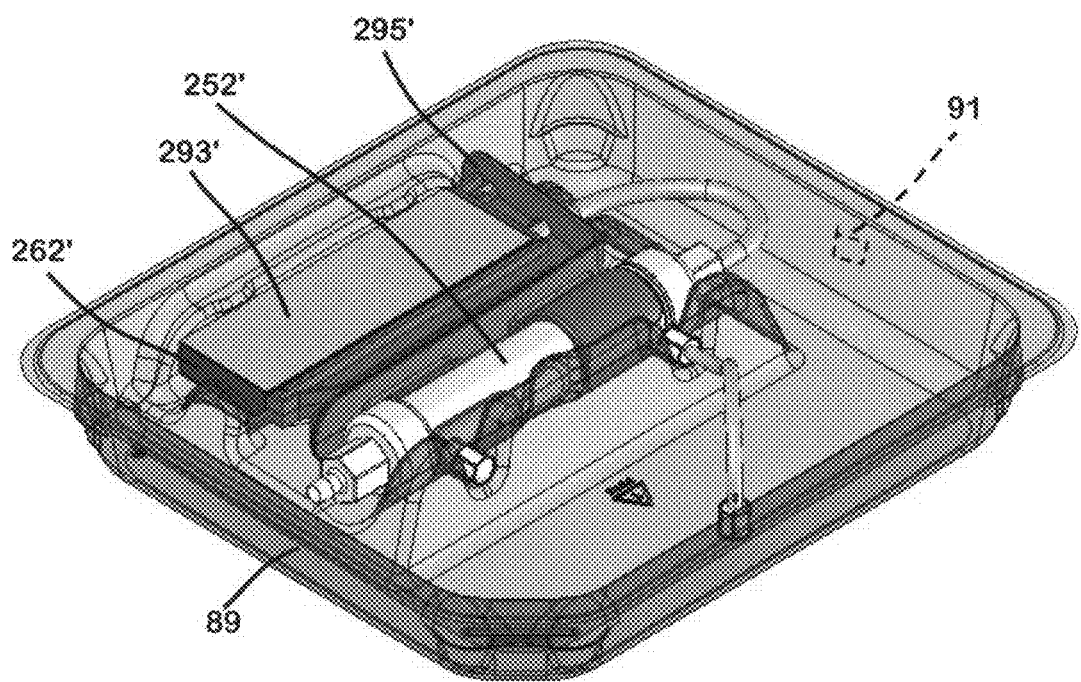
FIG. 11 is a perspective view of at least a portion of the fluid management system of one embodiment of the presently disclosed technology in a tray or kit.

In one embodiment, the components described herein can be packaged in a tray or container 89 (see FIG. 11) as a kit. The single-use, single-loop fluid loop kit for therapeutic ultrasound applications of the presently disclosed technology is simple to install, prime, use, and dispose of. Additional features can include a compact implementation, compatibility with gamma sterilization, cost-effective single-use components for temperature and dissolved gas content handling, and provisions for a simple and unambiguous user installation and kit installation detection.

The single loop, closed loop, single-use fluid path of one embodiment of the presently disclosed technology can incorporate one or more of the following components: the plurality of conduits or interconnect tubing, an inline degasser cartridge 52', 152', 252', an inline heat exchanger block 62', 162', 262', a fluid reservoir 82', 182', 282' (empty or pre-filled) with one or more connection spikes 192', 292', a tray 89 with label, and one or more identification devices (as described in detail below). The single loop can minimize interconnection points (and potential failure points) for components. The single loop can also increase degassing and temperature exchange efficiencies, minimize component counts, and/or simplify user installation of the kit in the appropriate water management system.

Optionally, free ends of each fluid conduit can have a simple and/or flexible connection point to facilitate connection of the various components of the system. In one embodiment, a first end of the single fluid conduit can include a male interconnection tip and a second end of the single fluid conduit can include a female interconnection tip. The first end can be configured to connect to a fluid inlet of a transducer assembly or a bolus assembly, and the second end can be configured to connect to the fluid outlet of the transducer assembly or the bolus assembly. These male and female components can help prevent the user from accidentally reversing the fluid inlet/outlet port connections, ensuring that the fluid loop is installed and connected correctly. In one embodiment, one or more of the plurality of fluid conduits can include peristaltic pump tubing sections, which can readily indicate to the user how the fluid loop is to be installed in the fluid management system. Optionally, these sections can have a different or unique color or pattern to reduce ambiguity, and can be sized and positioned within the complete fluid path as to only be able to be installed in one way/position.

More specifically, as shown in FIG. 6, the plurality of conduits or interconnect tubing can contain one or more separable sections. For example, the first conduit 132' can include a middle conduit 132b' connecting a first end conduit 132a' and a second end conduit 132c'. Optionally, each end of the middle conduit 132b' can include a male projection configured to extend at least slightly into one of the first and second end conduits 132a', 132b'. The second conduit 134' can include a corresponding and similarly arranged first end conduit 134a', middle conduit 134b', and second end conduit 134c'. In one embodiment, some or all of the conduits (or one or more sections thereof) can be made out of a silicone rubber material, which are compatible with peristaltic pumps. The silicone rubber can be peroxide cured. Optionally, some or all of the conduits (or one or more sections thereof) can be made out of vinyl or polyvinyl chloride (PVC) tubing. The portions (e.g., the middle conduits 132b', 134b' can be particularly suited for contact with at least a portion of a peristaltic pump.

The loop or plurality of fluid conduits can be designed to be disposable or for single-use. This is reflected in the simplicity of the design. In one embodiment, this single-use functionality can be controlled via one or more identification device(s), as described in detail below. In one embodiment, the single-loop implementation of the presently disclosed technology enables a simple set-up, use, and and/or teardown of the fluid loop. For example, in one embodiment, the user only needs to make or disconnect five connections: two to the probe, two to the fluid reservoir, and one for the vacuum line of the degasser cartridge. After placing two tubing in the appropriate pump heads and placing the fluid reservoir on a hook, for example, the system is installed and ready for use.

The loop and/or the kit can be designed to be compatible with gamma sterilization. This can be accomplished via the choice of materials and components (e.g., nylon or polycarbonate for the plastics, aluminum for the heat exchanger, etc.), and testing to verify that the sterilization process does not change the properties, functionality, color, etc. of the other components of the kit.

In one embodiment, the degassing cartridge 52', 152', 252' is able to remove dissolved gases from the circulating fluid (e.g., sterile water) via semi-permeable hydrophilic tubing and an externally-applied vacuum. Degassing of the circulating fluid is typically required in therapeutic systems to prevent dissolved gases and bubbles from interfering with and disturbing the propagation of the ultrasonic waves from the transducer through the circulating/coupling fluid and into the target tissue. The heat exchanger 62', 162', 262' can be configured to cool and/or heat the circulation fluid via the external contact of an energy source (such as a thermo-electric cooling element) to its surface. Conductivity between the thermo-electric element and the heat exchanger can be enhanced by thermally-conductive pads 193', 293' applied to both sides of the heat-exchanger 62', 162', 262'. The heat-exchanger 62', 162', 262' can be constructed out of a heat-conductive material, such as aluminum, and can circulate the fluid through its interior in a meandering channel so as to maximize the heat-exchange process.

Referring to FIGS. 6-10, a cartridge holder or carrier 195', 295' can hold or support both the degasser cartridge 152', 252' and the heat-exchanger 62', 162', 262'. In one embodiment, the carrier 195', 295' can pre-connect the degasser cartridge 152', 252' and the heat-exchanger 62', 162', 262', thereby simplifying user installation of this assembly. Optionally, the shape of the carrier 195', 295' can be such that it mates with or fits at least partially into to an appropriate slot in the housing 90 of the fluid management system 30, thereby providing a solid tactile feedback to the user that the carrier 195', 295' is installed correctly. As shown in FIG. 8, the carrier 295' can have two or more spaced-apart cutouts 296' that allow the degasser cartridge 252' to rotate (e.g., by 90 degrees) within the carrier 295'. This allows for generating a fluid loop that can be packaged in the tray 89 or other packing structure (i.e. bag or pouch) with a lower profile than otherwise possible, thereby streamlining the packaging requirements.

The single-use feature can be enabled and/or controlled via the use of one or more identification devices 91 (as shown schematically in FIG. 11), such as read/write RFID tag and specific usage algorithm, which can be used for tracking manufacturing, quality, and end-user usage information. In an alternative embodiment, other technologies could be used instead of RFID, such as barcode (1D/2D), a physical key, a memory card, credit-card-like device with chip, etc. These and other technologies can be used to prevent, or at least limit the likelihood of, more than one use of the system.

For example, in one embodiment, at least one RFID tag can ensure (in combination with the coupling fluid management system) that the fluid loop is used only once. To accomplish this, each fluid loop kit can contain a (e.g., gamma-compatible) RFID tag, pre-programmed with a unique identification (ID) code. The RFID tag may include additional information, such as manufacturing date/time, lot, location, etc. During installation of the fluid loop the user is requested to scan the RFID tag of the container 89 with a RFID reader/writer subsystem. In one embodiment, the RFID subsystem will first read the ID code, and compare it to other previously scanned IDs (e.g., stored it in its non-volatile memory). If the RFID subsystem does not find a match (indicating that this kit has not been previously used with this particular coupling fluid management system), it will add this ID to the list of previously scanned IDs in its non-volatile memory, and immediately write a unique 'read word' back into the RFID's memory. This 'read word' is derived from the ID itself, a value encoding the unique serial number of the coupling fluid management system, and a time stamp. If this operation is successful, the controller and/or the coupling fluid management system will enable all of its functions, and allow the user to proceed with the use of this kit as part of a therapeutic application. If this kit (and its associated RFID tag) is now scanned by a different coupling fluid management system, it will detect that the tag not only contains its original ID, but also the additional information written to it by the previous system. If this occurs, the new coupling fluid management system will prevent this kit from being used again, thus managing fraudulent and non-single-use use. If this kit (and associated RFID tag) is scanned by the same system again (thus finding the kits ID stored in its non-volatile memory, the system will request the timestamp information from the RFID tag. If the timestamp is within a certain pre-set time-limit (such as 4 hours, for example), all coupling fluid management system functions will continue to be available. This feature allows for re-use of the existing kit in extenuating circumstances, like an unintended power failure, which signifies a legitimate need to rescan the kit. Alternate security algorithms can be enabled by the use of the RFID tag, such as those based on time (as described above), number of uses (e.g., 1, 2, . . . infinite), locking certain kits to be used with specific coupling fluid management systems (based on their serial number), and/or other applications.

In one embodiment, the RFID tag 91 is gamma-compatible, so that it can be placed inside the tray 89 during manufacturing to reduce the handling necessary if the tag had to be applied post-sterilization. Affixing the RFID tag 91 to the inside of the tray using an adhesive further physically restricts the tag to that specific kit, minimizing additional fraud.

The carrier 195', 295' or any other portion of the system can include a component or feature that indicates to a user that the carrier 195', 295' has been installed properly in and/or attached to the fluid management system. For example, as shown in FIG. 6, the carrier 195' can include a projection 197' extending at least slightly outwardly therefrom. At least a portion of the projection 197' can break or at least slightly interrupt a beam of light located inside or directed at the system. In operation, this feature can be used by the system to indicate that the carrier (and thus the degasser cartridge and the heat exchange block) has been correctly installed by the user, and is ready to be used by the fluid management system and/or the controller. In one embodiment, an optical detection mechanism is preferred in order to avoid carrier installation detection degradation as a function of time and associated dust, dirt, mechanical wear and tear, etc. However, the presently disclosed technology is not limited to only using an optical detection mechanism, as other technologies may be employed.

In one embodiment, one or more of the fluid conduits can include spikes, tips or valves. For example, as shown in FIG. 7, two of the fluid conduits can include spikes 192' to connect to the fluid reservoir. In another embodiment, as shown in FIG. 8, one of the fluid conduits can include a single spike 292' to connect to the fluid reservoir. The spikes enable easy or simple connection and disconnection of various portions of the system. In one embodiment, almost all or most connections within the fluid loop can be implemented as barb fittings. In certain instances, barbed interconnections are preferred, as they maintain their connections through a gamma sterilization cycle (unlike luer-based connections, which can loosen), and tend to be better for managing potential leaks both into and out of the closed fluid loop.

The fluid loop can be compatible with an optional in-line dissolved gas detection system. This system can be placed at any position in the loop, and would be used to measure the dissolved gas content, to verify that the degassing system is in fact performing as expected. One appropriate location for the in-line dissolved gas detector would be at the output of the degasser cartridge 152', 252'. Suitable sensors could be those from PreSens Precision Sensing GmbH of Regensburg, Germany, or equivalent, as flow-through oxygen monitoring sensors are readily available (such as the Single-Use $O_2$ Flow-Through Cell FTC-SU-PSt3-S) that are compatible with the single-loop, single-use nature of the discussed fluid loop. The cost for this in-line implementation is reasonable and compatible with the single-use nature of this kit. The sensors single-use intent would not compromise the sterility of the circulating fluid.

In yet another embodiment, debubbling can be monitored using the vacuum level indicator of the fluid management system. In semi-permeable cartridge-based degassing systems, the vacuum level used for degassing dips briefly every time a bubble flows through the degasser cartridge, as the vacuum pump labors or works to restore the vacuum to its previous level prior to the bubble(s) having compromised it as it flows through the cartridge. By monitoring these dips over a predetermined amount of time, the system is able to detect when bubbles have ceased flowing through the degassing cartridge, and thus indicate that the debubbling step is complete.

Optionally, the fluid loop can be compatible with a fluid flow detection system. This system can be placed at any position in the loop, and would be used to measure the fluid flow, and to verify that the pumping system is in fact circulating the coupling fluid as expected. An appropriate location for the flow detection detector would be at any place along the interconnection tubing. Suitable fluid flow detectors could be those from Transonic Systems Inc. of Ithaca, N.Y., such as their PXL Clamp-On Bioprocess Flowsensor (or equivalent), which are available in a correct size to attach to the outside of the interconnection tubing. This sensor would not compromise the sterility of the circulating fluid.

As another option, the fluid loop can be compatible with a bubble detection system. This system can be placed at any position in the loop, and would be used to determine if air bubbles are circulating within the loop. Ideally, all air bubbles (and dissolved gases) would be removed prior to its use in a therapeutic application, as air in the coupling fluid can detrimentally affect the propagation of the ultrasonic energy from the probe to the target tissue. An appropriate location for the bubble detection detector would be at any place along the interconnection tubing that carries fluid towards the probe assembly. Suitable bubble detectors could be those from Transonic Systems Inc., such as their PXL Clamp-On Bioprocess Flowsensor (or equivalent), which are available in a correct size to attach to the outside of the interconnection tubing. This sensor would not compromise the sterility of the circulating fluid.

3. Embodiments of Computer System

Figure 12:
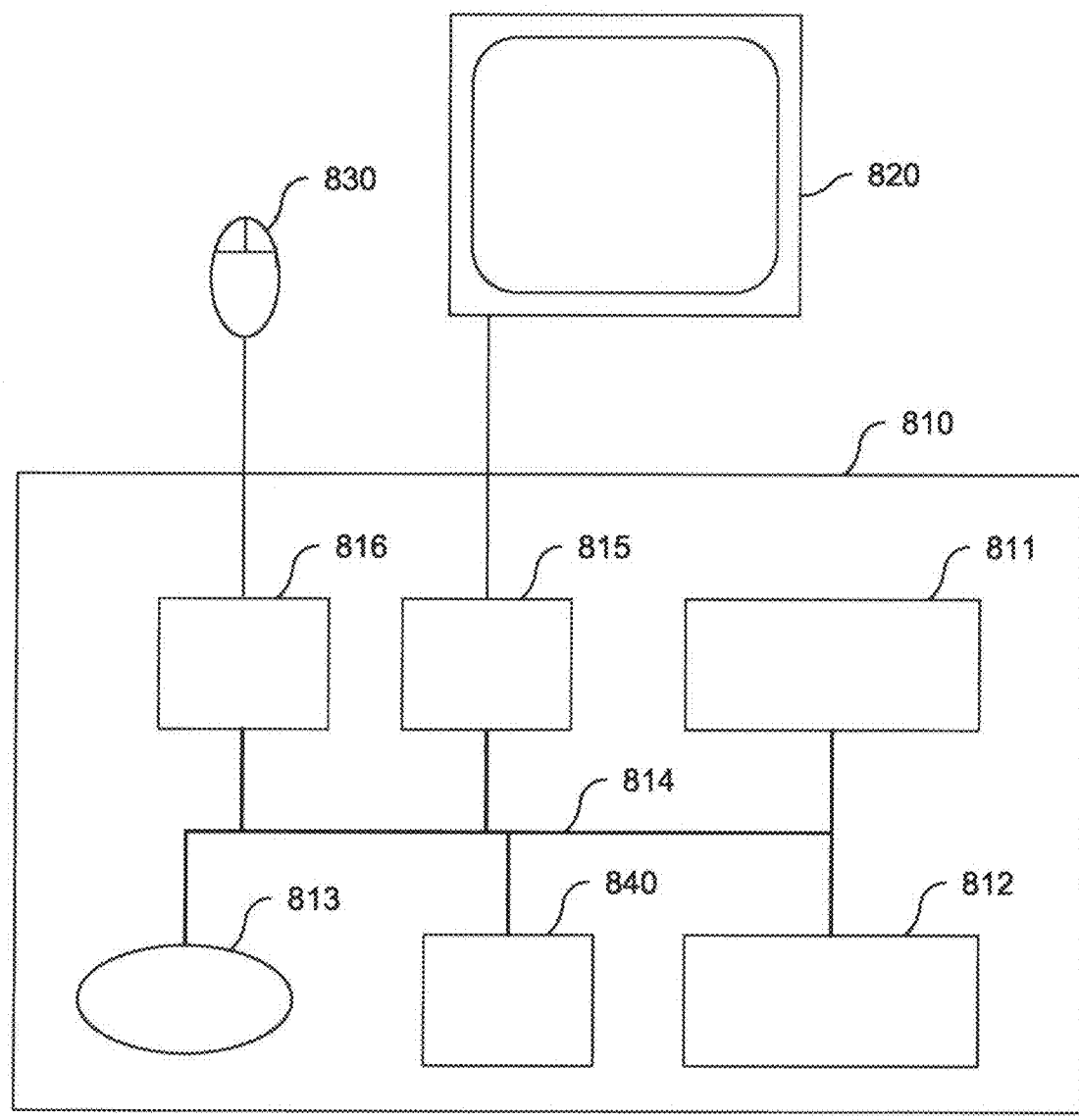
FIG. 12 is a schematic diagram of a computing system of one embodiment of the present disclosure.

One or more of the above-described techniques and/or embodiments can be implemented with or involve software, for example modules executed on one or more computing devices 810 (see FIG. 12). Of course, modules described herein illustrate various functionalities and do not limit the structure or functionality of any embodiments. Rather, the functionality of various modules may be divided differently and performed by more or fewer modules according to various design considerations.

Each computing device 810 may include one or more processing devices 811 designed to process instructions, for example computer readable instructions (i.e., code), stored in a non-transient manner on one or more storage devices 813. By processing instructions, the processing device(s) 811 may perform one or more of the steps and/or functions disclosed herein. Each processing device may be real or virtual. In a multi-processing system, multiple processing units may execute computer-executable instructions to increase processing power.

The storage device(s) 813 may be any type of non-transitory storage device (e.g., an optical storage device, a magnetic storage device, a solid state storage device, etc.). The storage device(s) 813 may be removable or non-removable, and may include magnetic disks, magneto-optical disks, magnetic tapes or cassettes, CD-ROMs, CD-RWs, DVDs, BDs, SSDs, or any other medium which can be used to store information. Alternatively, instructions may be stored in one or more remote storage devices, for example storage devices accessed over a network or the internet.

Each computing device 810 additionally may have memory 812, one or more input controllers 816, one or more output controllers 815, and/or one or more communication connections 840. The memory 812 may be volatile memory (e.g., registers, cache, RAM, etc.), non-volatile memory (e.g., ROM, EEPROM, flash memory, etc.), or some combination thereof. In at least one embodiment, the memory 812 may store software implementing described techniques.

An interconnection mechanism 814, such as a bus, controller or network, may operatively couple components of the computing device 810, including the processor(s) 811, the memory 812, the storage device(s) 813, the input controller(s) 816, the output controller(s) 815, the communication connection(s) 840, and any other devices (e.g., network controllers, sound controllers, etc.). The output controller(s) 815 may be operatively coupled (e.g., via a wired or wireless connection) to one or more output devices 820 (e.g., a monitor, a television, a mobile device screen, a touch-display, a printer, a speaker, etc.) in such a fashion that the output controller(s) 815 can transform the display on the output device 820 (e.g., in response to modules executed). The input controller(s) 816 may be operatively coupled (e.g., via a wired or wireless connection) to one or more input devices 830 (e.g., a mouse, a keyboard, a touch-pad, a scroll-ball, a touch-display, a pen, a game controller, a voice input device, a scanning device, a digital camera, etc.) in such a fashion that input can be received from a user.

The communication connection(s) 840 may enable communication over a communication medium to another computing entity. The communication medium conveys information such as computer-executable instructions, audio or video information, or other data in a modulated data signal. A modulated data signal is a signal that has one or more of its characteristics set or changed in such a manner as to encode information in the signal. By way of example, and not limitation, communication media include wired or wireless techniques implemented with an electrical, optical, RF, infrared, acoustic, or other carrier.

FIG. 12 illustrates the computing device 810, the output device 820, and the input device 830 as separate devices for ease of identification only. However, the computing device 810, the output device(s) 820, and/or the input device(s) 830 may be separate devices (e.g., a personal computer connected by wires to a monitor and mouse), may be integrated in a single device (e.g., a mobile device with a touch-display, such as a smartphone or a tablet), or any combination of devices (e.g., a computing device operatively coupled to a touchscreen display device, a plurality of computing devices attached to a single display device and input device, etc.). The computing device 810 may be one or more servers, for example a farm of networked servers, a clustered server environment, or a cloud service running on remote computing devices.

In one embodiment, the presently disclosed technology is directed to a non-transitory computer-readable medium having computer-readable code stored thereon that, when executed by one or more computing devices, causes the one or more computed devices to perform the one or more methods disclosed or claimed herein.

4. Recitation of Exemplary Embodiments

The following exemplary embodiments further describe optional aspects of the presently disclosed technology and are part of this Detailed Description. These exemplary embodiments are set forth in a format substantially akin to claims (each with numerical designations followed by the letter A), although they are not technically claims of the present application. The following exemplary embodiments refer to each other in dependent relationships as "embodiments" instead of "claims."

1A. A therapeutic or diagnostic ultrasound system comprising a fluid management system fluidly connected to an ultrasound probe assembly, the fluid management system comprising:
  a plurality of conduits forming a single circuit and comprising a first conduit and a second conduit each configured to extend from and be fluidly connected to an ultrasound probe assembly;
  a fluid directing system comprising a first pump fluidly connected to both the first conduit and the second conduit in order to circulate a fluid into and out of the ultrasound probe assembly, the first pump being a circulation pump;
  a fluid degassing system fluidly connected to the first and second conduits, the fluid degassing system being configured to remove at least some gas from the fluid in the ultrasound probe assembly;
  a temperature control system fluidly connected to the first and second conduits, the temperature control system being configured to control the temperature of the fluid in the ultrasound probe assembly; and
  a volume adjustment system fluidly connected to the first and second conduits, the volume adjustment system being configured to adjust the volume of the fluid in the ultrasound probe assembly.

2A. The system of embodiment 1A, wherein the volume adjustment system includes a deformable bladder.

3A. A coupling fluid management system, comprising:
  a single-loop, closed loop fluid path, comprising:
    interconnect tubing,
    at least one pump,
    an inline degasser cartridge operatively connected to a vacuum pump,
    an inline heat exchanger block,
    a fluid reservoir, and
    an optional inline oxygen sensor;
  a cooling and/or heating system operatively connected to the inline heat exchanger block;
  a temperature sensor;
  a fluid degassing system operatively connected to the inline degasser cartridge, comprising:
    a vacuum pump,
    a vacuum sensor; and
  a fluid volume adjustment system operatively connected to the fluid reservoir.

4A. The system of embodiment 3A, further comprising a controller which operates using a control algorithm to control the at least one pump, the cooling and/or heating system, the fluid degassing system and the fluid volume adjustment system, and configured to receive input from the optional inline oxygen sensor, temperature sensor and vacuum sensor.

5A. A fluid management system for use with an ultrasound probe assembly, the system comprising:
  a plurality of conduits forming a single circuit and comprising a first conduit and a second conduit each configured to extend from and be fluidly connected to an ultrasound probe assembly;
  a fluid directing system comprising a first pump fluidly connected to both the first conduit and the second conduit in order to circulate a fluid into and out of the ultrasound probe assembly, the first pump being a circulation pump;
  a fluid degassing system fluidly connected to the first and second conduits, the fluid degassing system being configured to remove at least some gas from the fluid in the ultrasound probe assembly, the fluid degassing system comprising a degasser module and a vacuum pump coupled to the degasser module, the vacuum pump being configured to draw gas out of the degasser module, the degasser module being fluidly connected to the first pump;
  a temperature control system fluidly connected to the first and second conduits, the temperature control system being configured to control the temperature of the fluid in the ultrasound probe assembly; and
  a volume adjustment system fluidly connected to the first and second conduits, the volume adjustment system being configured to adjust the volume of the fluid in the ultrasound probe assembly.

6A. The system of embodiment 5A, wherein the first conduit is configured to extend between the degasser module and the ultrasound probe assembly.

7A. The system of embodiment 5A, wherein the fluid degassing system further comprises a vacuum sensor coupled to the degasser module.

8A. The system of embodiment 5A, wherein the temperature control system comprises a heat exchanger module fluidly connected to the first pump.

9A. The system of embodiment 8A, wherein the temperature control system further comprises a heating/cooling element coupled to the heat exchanger module.

10A. The system of embodiment 9A, wherein the heating/cooling element is selected from the group consisting of a thermoelectric element, a resistive heating element, and a refrigeration system.

11A. An ultrasound system comprising:
  an ultrasound probe assembly comprising a transducer assembly and a bolus assembly, the bolus assembly surrounding at least a portion of the transducer assembly; and a fluid management system comprising:
  a plurality of conduits comprising a first conduit and a second conduit each extending from and being fluidly connected to the ultrasound probe assembly;
  a fluid directing system comprising a first pump fluidly connected to both the first conduit and the second conduit in order to circulate a fluid into and out of the ultrasound probe assembly, the first pump being a circulation pump;
  a fluid degassing system fluidly connected to the first conduit and second conduits, the fluid degassing system being configured to remove at least some gas from the fluid in the ultrasound probe assembly;
  a temperature control system fluidly connected to the first and second conduits, the temperature control system being configured to control the temperature of the fluid in the ultrasound probe assembly, the temperature control system comprising a temperature sensor, a heating/cooling element, and a heat exchanger module coupled to the heating/cooling element, the heat exchanger module being fluidly connected to the circulation pump; and
  a volume adjustment system fluidly connected to the first and second conduits, the volume adjustment system being configured to adjust the volume of the fluid in the ultrasound probe assembly,
wherein the temperature sensor is connected to the ultrasound probe assembly and is configured to cooperate with the heating/cooling element in order to control the temperature of the fluid in the ultrasound probe assembly.

12A. The system of embodiment 11A, wherein the fluid management system further comprises a controller, and wherein the controller employs an algorithm to control the fluid directing system, the fluid degassing system, the temperature control system, and the volume adjustment system.

13A. The system of embodiment 11A, wherein the temperature sensor is connected with at least one of the transducer assembly and the bolus assembly.

14A. A system for treating tissue, the system comprising:
  a plurality of fluid conduits forming a single fluid circuit, the single fluid circuit having a first end and an opposing second end, the first end of the single fluid circuit being configured to fluidly connect to a fluid inlet of an ultrasound probe assembly, the second end of the single fluid circuit being configured to fluidly connect to a fluid outlet of the ultrasound probe assembly;
  a fluid degassing system positioned within the single fluid circuit, the fluid degassing system being configured to remove at least some gas from fluid circulated in the single fluid circuit; and
  a temperature control system positioned within the single fluid circuit, the temperature control system being configured to control the temperature of the fluid circulated in the single fluid circuit.

15A. The system of embodiment 14A, wherein the plurality of fluid conduits include a first fluid conduit, a second fluid conduit, a third fluid conduit, a fourth fluid conduit and a fifth fluid conduit, each of the first, second, third, fourth and fifth fluid conduits being fluidly connected to form the single fluid circuit.

16A. The system of embodiment 14A, wherein a first fluid conduit of the plurality of fluid conduits fluidly connects the fluid inlet of the ultrasound probe assembly to one of the fluid degassing system and a pump positioned within the single fluid circuit, wherein a second fluid conduit of the plurality of fluid conduits fluidly connects the fluid outlet of the ultrasound probe assembly to at least one of a fluid reservoir and the temperature control system, and wherein a third fluid conduit of the plurality of fluid conduits fluidly connects the fluid degassing system to the temperature control system.

17A. The system of embodiment 16A, wherein a fourth fluid conduit of the plurality of fluid conduits fluidly connects a degasser module and a vacuum pump, the vacuum pump being configured to draw at least some gas out of the degasser module.

18A. The system of embodiment 17A, wherein a fifth fluid conduit of the plurality of fluid conduits fluidly connects the temperature control system to the fluid reservoir.

19A. The system of embodiment 14A, further comprising a carrier configured to engage or hold both at least a portion of the fluid degassing system and at least a portion of the temperature control system.

20A. A system for treating tissue, the system comprising:
  a fluid loop system fluidly connected to an ultrasound probe assembly, the fluid loop system including:
    a plurality of fluid conduits forming a single fluid circuit, the single fluid circuit having a first end and an opposing second end, the first end of the single fluid circuit being configured to fluidly connect to a fluid inlet of the ultrasound probe assembly, the second end of the single fluid circuit being configured to fluidly connect to a fluid outlet of the ultrasound probe assembly;
    a fluid degassing system positioned within or attached to the single fluid circuit, the fluid degassing system being configured to remove at least some gas from fluid circulated in the single fluid circuit; and
    a temperature control system positioned within the single fluid circuit, the temperature control system being configured to control the temperature of the fluid circulated in the single fluid circuit; and
  a container including an identification device, the container being configured to hold or support at least some of the plurality of fluid conduits, the fluid degassing system, and the temperature control system,
wherein the identification device is selected from the group consisting of a (i) radio-frequency identification (RFID) tag affixed to a portion of the container, (ii) a barcode affixed to or inscribed in a portion of the container, (iii) a memory card affixed to a portion of the container, (iv) a key attached to a portion of the container, and (v) a chip attached to a portion of the container.

21A. The system of embodiment 20A, further comprising:
  one or more processors; and
  one or more memories operatively coupled to the one or more processors and having computer readable instructions stored thereon which, when executed by at least one of the one or more processors, causes the at least one of the one or more processors to:
    a) receive information obtained from the identification device;
    b) compare the received information to a database of stored information;
    c) if the received information does not match at least a portion of the stored information, add the received information to the database of stored information; and
    d) if the received information matches at least a portion of the stored information, transmit a signal configured to indicate that the fluid loop system has been previously used.

22A. The system of embodiment 20A, wherein the identification device is the RFID tag, the RFID tag being gamma compatible, the RFID tag being pre-programmed with at least a unique identification code, the RFID tag being affixed to an inside surface of the container.

23A. The system of embodiment 20A, further comprising:
a fluid directing system positioning within or attached to the single fluid circuit, the fluid directing system comprising a first pump in the form of a circulation pump, the circulation pump being configuration to circulate fluid into and out of the ultrasound probe assembly through the fluid inlet and outlet, respectively; and
a volume adjustment system positioning within the single fluid circuit, the volume adjustment system being configured to adjust the volume of the fluid in the ultrasound probe assembly, the volume adjustment system including a fluid reservoir.

The above disclosed systems, apparatuses, methods and description of generic embodiments of the presently disclosed technology are provided to enable any person skilled in the art to make or use the invention. Various modifications to the embodiments described herein will be readily apparent to those skilled in the art, and the generic principles described herein can be applied to other embodiments without departing from the spirit or scope of the presently disclosed technology. Thus, it is to be understood that the description and drawings presented herein represent a functional generic embodiment of the presently disclosed technology and are, therefore, representative of the subject matter which is broadly contemplated by the presently disclosed technology. It is further understood that the scope of the presently disclosed technology fully encompasses other embodiments that may become obvious to those skilled in the art and that the scope of the presently disclosed technology is accordingly limited by nothing other than the appended claims.

We claim:

1. A fluid management system for use with an ultrasound probe assembly, the system comprising:
   a plurality of conduits forming a single circuit and comprising a first conduit and a second conduit each configured to extend from and be fluidly connected to an ultrasound probe assembly;
   a fluid directing system comprising a first pump fluidly connected to both the first conduit and the second conduit in order to circulate a fluid into and out of the ultrasound probe assembly, the first pump being a circulation pump;
   a fluid degassing system fluidly connected to the first and second conduits, the fluid degassing system being configured to remove at least some gas from the fluid in the ultrasound probe assembly;
   a temperature control system fluidly connected to the first and second conduits, the temperature control system being configured to control the temperature of the fluid in the ultrasound probe assembly; and
   a volume adjustment system fluidly connected to the first and second conduits, the volume adjustment system being configured to adjust the volume of the fluid in the ultrasound probe assembly, the volume adjustment system comprising a fluid reservoir and a second pump fluidly connected to the fluid reservoir, the fluid reservoir being a deformable bladder, the second pump being configured to selectively rotate clockwise or counterclockwise to control fluid volume addition or removal to the ultrasound probe assembly, the second pump being located within the second conduit and between the fluid reservoir and the ultrasonic probe assembly.

2. The fluid management system of claim 1, wherein the fluid degassing system comprises a degasser module and a vacuum pump coupled to the degasser module, wherein the vacuum pump is configured to draw gas out of the degasser module, and wherein the degasser module is fluidly connected to the first pump.

3. The fluid management system of claim 2, wherein the temperature control system comprises a heat exchanger module fluidly connected to the first pump, wherein the temperature control system further comprises a heating/cooling element coupled to the heat exchanger module, wherein the temperature control system further comprises a plurality of temperature sensors each coupled to one of the plurality of conduits, the fluid degassing system, and the volume adjustment system, and wherein each of the temperature sensors cooperates with the heat exchanger module to control temperature of the fluid in the ultrasound probe assembly.

4. The fluid management system of claim 2, wherein the temperature control system comprises a heat exchanger module fluidly connected to the first pump.

5. The fluid management system of claim 4, wherein the first conduit is configured to extend between the ultrasound probe assembly and one of the degasser module and the first pump.

6. The fluid management system of claim 5, wherein the plurality of conduits further comprises a third conduit, wherein the third conduit extends between the volume adjustment pump and the fluid reservoir, and wherein the volume adjustment pump is configured to inject gas into and remove gas from the fluid reservoir to thereby add fluid into and remove fluid from the ultrasound probe assembly, respectively.

7. The fluid management system of claim 4, wherein the first conduit is configured to extend between the ultrasound probe assembly and one of the degasser module and the first pump, and wherein the plurality of conduits further comprises a third conduit extending between the second pump and the fluid reservoir.

8. The fluid management system of claim 4, wherein the plurality of conduits further comprises a third conduit extending between the second pump and the fluid reservoir, wherein the fluid management system includes only one single conduit extending from the fluid reservoir and being configured to be fluidly connected to the first conduit and the second conduit, and wherein the only one single conduit is the third conduit.

9. The fluid management system of claim 4, wherein the volume adjustment system further comprises a weight measurement system coupled to the fluid reservoir, and wherein the weight measurement system is configured to measure the weight of the fluid in the fluid reservoir.

10. An ultrasound system comprising:
    an ultrasound probe assembly comprising a transducer assembly and a bolus assembly, the bolus assembly surrounding at least a portion of the transducer assembly; and
    a fluid management system comprising:
      a plurality of conduits comprising a first conduit and a second conduit each extending from and being fluidly connected to the ultrasound probe assembly;
      a fluid directing system comprising a first pump fluidly connected to both the first conduit and the second conduit in order to circulate a fluid into and out of the ultrasound probe assembly, the first pump being a circulation pump;
      a fluid degassing system fluidly connected to the first conduit and second conduits, the fluid degassing system being configured to remove at least some gas from the fluid in the ultrasound probe assembly;

a temperature control system fluidly connected to the first and second conduits, the temperature control system being configured to control the temperature of the fluid in the ultrasound probe assembly, the temperature control system comprising a temperature sensor, a heating/cooling element, and a heat exchanger module coupled to the heating/cooling element, the heat exchanger module being fluidly connected to the circulation pump; and a volume adjustment system fluidly connected to the first and second conduits, the volume adjustment system being configured to adjust the volume of the fluid in the ultrasound probe assembly, the volume adjustment system comprising a fluid reservoir and a second pump fluidly connected to the fluid reservoir, the fluid reservoir being a deformable bladder, the second pump being a volume adjustment pump, the second pump being configured to selectively rotate clockwise or counterclockwise to control fluid volume addition or removal to the ultrasound probe assembly, the second pump located within the second conduit and between the fluid reservoir and the ultrasonic probe assembly, wherein the temperature sensor is connected to the ultrasound probe assembly and is configured to cooperate with the heating/cooling element in order to control the temperature of the fluid in the ultrasound probe assembly.

11. The ultrasound system of claim 10, wherein the fluid degassing system comprises a degasser module and a vacuum pump coupled to the degasser module, wherein the degasser module is fluidly connected to the first pump, and wherein the first conduit extends between the ultrasound probe assembly and one of the degas ser module and the first pump.

12. The ultrasound system of claim 11, wherein the plurality of conduits further comprises a third conduit extending between the second pump and the fluid reservoir.

13. A system for treating tissue, the system comprising:
a plurality of fluid conduits forming a single fluid circuit, the single fluid circuit having a first end and an opposing second end, the first end of the single fluid circuit being configured to fluidly connect to a fluid inlet of an ultrasound probe assembly, the second end of the single fluid circuit being configured to fluidly connect to a fluid outlet of the ultrasound probe assembly;
a fluid degassing system positioned within the single fluid circuit, the fluid degassing system being configured to remove at least some gas from fluid circulated in the single fluid circuit; and
a temperature control system positioned within the single fluid circuit, the temperature control system being configured to control the temperature of the fluid circulated in the single fluid circuit, and
a container including a radio-frequency identification (RFID) tag affixed to an inside surface thereof, the container being configured to hold or support at least some of the plurality of fluid conduits, the fluid degassing system, and the temperature control system,
wherein the RFID tag is gamma sterilization compatible and pre-programmed with at least a unique identification code.

14. The system of claim 13, further comprising:
a volume adjustment system fluidly connected to the single fluid circuit by a conduit, the volume adjustment system being configured to adjust the volume of the fluid in the ultrasound probe assembly, the volume adjustment system including a fluid reservoir.

15. The system of claim 13, further comprising:
a volume adjustment system positioning within the single fluid circuit, the volume adjustment system being configured to adjust the volume of the fluid in the ultrasound probe assembly, the volume adjustment system including a fluid reservoir.

16. The system of claim 13, wherein a first fluid conduit of the plurality of fluid conduits fluidly connects the fluid inlet of the ultrasound probe assembly to one of the fluid degassing system and a pump positioned within the single fluid circuit, and wherein a second fluid conduit of the plurality of fluid conduits fluidly connects the fluid outlet of the ultrasound probe assembly to at least one of a fluid reservoir and the temperature control system.

17. The system of claim 13, further comprising:
a fluid directing system positioning within or attached to the single fluid circuit, the fluid directing system comprising a first pump in the form of a circulation pump, the circulation pump being configuration to circulate fluid into and out of the ultrasound probe assembly through the fluid inlet and outlets, respectively.

18. A system for treating tissue, the system comprising:
an ultrasound probe assembly including a transducer assembly and a bolus assembly, the transducer assembly including at least one transducer located proximate an end of a shaft, the bolus assembly surrounding at least a portion of the at least one transducer of the transducer assembly, the ultrasound probe assembly having a fluid inlet and a fluid outlet; and
a fluid loop system fluidly connected to the ultrasound probe assembly, the fluid loop system including:
a plurality of fluid conduits forming a single fluid circuit, the single fluid circuit having a first end and an opposing second end, the first end of the single fluid circuit being configured to fluidly connect to the fluid inlet of the ultrasound probe assembly, the second end of the single fluid circuit being configured to fluidly connect to the fluid outlet of the ultrasound probe assembly;
a fluid degassing system positioned within the single fluid circuit, the fluid degassing system being configured to remove at least some gas from fluid circulated the single fluid circuit; and
a temperature control system positioned within the single fluid circuit, the temperature control system being configured to control the temperature of the fluid circulated in the single fluid circuit, and
a container including an identification device, the container being configured to hold or support at least some of the plurality of fluid conduits, the fluid degassing system, and the temperature control system,
wherein the identification device is selected from the group consisting of a (i) radio-frequency identification (RFID) tag affixed to a portion of the container, (ii) a barcode affixed to or inscribed in a portion of the container, (iii) a memory card affixed to a portion of the container, (iv) a key attached to a portion of the container, and (v) a chip attached to a portion of the container.

19. The system of claim 18, wherein the fluid loop system further comprises:
a volume adjustment system positioned within the single fluid circuit, the volume adjustment system being configured to adjust the volume of the fluid in the ultrasound probe assembly, the volume adjustment system including a fluid reservoir.

20. The system of claim 18, wherein the fluid loop system further comprises:
a fluid directing system positioned within or attached to the single fluid circuit, the fluid directing system being configured to circulate a fluid into and out of the ultrasound probe assembly, the first pump being a circulation pump.

21. The system of claim 18, further comprising:
one or more processors; and
one or more memories operatively coupled to the one or more processors and having computer readable instructions stored thereon which, when executed by at least one of the one or more processors, causes the at least one of the one or more processors to:

a) receive information obtained from the identification device;
b) compare the received information to a database of stored information;
c) if the received information does not match at least a portion of the stored information, add the received information to the database of stored information; and
d) if the received information matches at least a portion of the stored information, transmit a signal configured to indicate that the fluid loop system has been previously used.

22. The system of claim 18, wherein the identification device is the RFID tag, the RFID tag being gamma compatible, the RFID tag being pre-programmed with at least a unique identification code, the RFID tag being affixed to an inside surface of the container.

* * * * *